United States Patent
Charych et al.

(10) Patent No.: US 11,318,164 B2
(45) Date of Patent: May 3, 2022

(54) IMMUNOTHERAPEUTIC TREATMENT METHOD USING AN INTERLEUKIN-2 RECEPTOR BETA-SELECTIVE AGONIST IN COMBINATION WITH ADOPTIVE CELL TRANSFER THERAPY

(71) Applicants: Nektar Therapeutics, San Francisco, CA (US); The Regents of the University of California, Oakland, CA (US)

(72) Inventors: Deborah H. Charych, Albany, CA (US); Antoni Ribas, Los Angeles, CA (US); Giulia Parisi, Los Angeles, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 16/490,443

(22) PCT Filed: Mar. 1, 2018

(86) PCT No.: PCT/US2018/020514
§ 371 (c)(1),
(2) Date: Aug. 30, 2019

(87) PCT Pub. No.: WO2018/160877
PCT Pub. Date: Sep. 7, 2018

(65) Prior Publication Data
US 2020/0016206 A1    Jan. 16, 2020

Related U.S. Application Data

(60) Provisional application No. 62/465,506, filed on Mar. 1, 2017, provisional application No. 62/480,971, filed on Apr. 3, 2017.

(51) Int. Cl.
| | | |
|---|---|---|
| *A61K 38/20* | (2006.01) | |
| *A61K 35/17* | (2015.01) | |
| *A61K 47/60* | (2017.01) | |
| *A61P 35/04* | (2006.01) | |

(52) U.S. Cl.
CPC .......... *A61K 35/17* (2013.01); *A61K 38/2013* (2013.01); *A61K 47/60* (2017.08); *A61P 35/04* (2018.01)

(58) Field of Classification Search
CPC .................................................. A61K 38/2013
See application file for complete search history.

(56) References Cited

U.S. PATENT DOCUMENTS

| | | | |
|---|---|---|---|
| 5,126,132 A | 6/1992 | Rosenberg | |
| 9,861,705 B2 * | 1/2018 | Bossard | A61P 31/14 |
| 10,960,079 B2 * | 3/2021 | Bossard | A61K 47/60 |
| 2014/0328791 A1 | 11/2014 | Bossard et al. | |

FOREIGN PATENT DOCUMENTS

| | | |
|---|---|---|
| WO | WO 2006/138572 A2 | 12/2006 |
| WO | WO 2012/065086 A1 | 5/2012 |
| WO | WO 2015/125159 A1 | 8/2015 |
| WO | WO 2015/143328 A1 | 9/2015 |
| WO | WO 2016/096903 A1 | 6/2016 |

OTHER PUBLICATIONS

Rosenberg et al, (1994), Journal of the National Cancer Institute, vol. 86, No. 15, pp. 1159-1166.*
Adotevi et al., "Targeting antitumor CD4 helper T cells with universal tumor-reactive helper peptides derived from telomerase for cancer vaccine", Human Vaccines & Immunotherapeutics, vol. 9, No. 5, pp. 1073-1077, (2013).
Ager et al., "31st Annual Meeting and Associated Programs of the Society for Immunotherapy of Cancer (SITC 2016): part two", Journal for Immunotherapy of Cancer, vol. 4, Suppl. 1, pp. 107-221, (2016).
Aranda et al., "Trial Watch: Adoptive cell transfer for anticancer immunotherapy", Trial Watch, OncoImmunology, vol. 3, No. 5, pp. e28344-1-e28344-13, (2014).
Berge et al., "Pharmaceutical Salts", Journal of Pharmaceutical Sciences, vol. 66, No. 1, pp. 1-19, (Jan. 1977).
Charych et al., "NKTR-214, an Engineered Cytokine with Biased IL2 Receptor Binding, Increased Tumor Exposure, and Marked Efficacy in Mouse Tumor Models", Clinical Cancer Research, vol. 22, No. 3, pp. 680-690, (Feb. 1, 2016).
Dudley et al., "Adoptive Cell Transfer Therapy", Seminars in Oncology, vol. 34, pp. 524-531, (2007).
Dudley et al., "Adoptive Cell Therapy for Patients With Metastatic Melanoma: Evaluation of Intensive Myeloablative Chemoradiation Preparative Regimens", Journal of Clinical Oncology, vol. 26, No. 32, pp. 5233-5239, (Nov. 10, 2008).
Dudley et al., "Adoptive Cell Transfer Therapy Following Non-Myeloablative but Lymphodepleting Chemotherapy for the Treatment of Patients With Refractory Metastatic Melanoma", Journal of Clinical Oncology, vol. 23, No. 10, pp. 2346-2357, (Apr. 1, 2005).
Grupp et al., "Chimeric Antigen Receptor-Modified T Cells for Acute Lymphoid Leukemia", N. Engl. J. Med., vol. 368, pp. 1509-1518, (2013).
Hershkovitz et al., "Focus on Adoptive T Cell Transfer Trials in Melanoma", Clinical and Developmental Immunology, vol. 2010, pp. 1-11, (2010).
Hinrichs et al., "Exploiting the curative potential of adoptive T-cell therapy for cancer", Immunological Reviews, vol. 257, pp. 56-71, (2014).
Kalos et al., "T Cells with Chimeric Antigen Receptors Have Potent Antitumor Effects and Can Establish Memory in Patients with Advanced Leukemia", Science Translational Medicine, vol. 3, Issue 95, pp. 1-11, (Aug. 10, 2011).

(Continued)

*Primary Examiner* — Prema M Mertz
(74) *Attorney, Agent, or Firm* — Susan T. Evans

(57) ABSTRACT

Provided are methods and compositions directed towards the treatment of an individual having cancer by providing adoptive cell transfer therapy and administering to the individual a long-acting IL-2Rβ-biased agonist.

25 Claims, 11 Drawing Sheets
Specification includes a Sequence Listing.

(56) References Cited

OTHER PUBLICATIONS

Langowski et al., "Abstract 558: Durable antitumor activity of the CD122-biased immunostimulatory cytokine NKTR-214 combined with immuno checkpoint blockade", Cancer Research, https://www.nektar.com/application/files/8114/7439/8270/CRI-CIMT-EATI-AACR_Poster.pdf, (Jul. 15, 2016).
Le et al., "Next-Generation Cancer Vaccine Approaches: Integrating Lessons Learned From Current Successes With Promising Biotechnologic Advances", Journal of the National Comprehensive Cancer Network, vol. 11, No. 7, pp. 766-772, (Jul. 2013).
Nektar Therapeutics 2016 JP Morgan Healthcare Conference, pp. 1-33, (Jan. 12, 2016).
Parisi et al., "Antitumor activity of NKTR-214 in combination with pmel-1 ACT in an aggressive murine melanoma model", Hall A-C, Poster section 26, AACR, Abstract #2671, Washington, D.C., (Apr. 3, 2017).
Phan et al., "Adoptive Cell Transfer for Patients With Metastatic Melanoma: The Potential and Promise of Cancer Immunotherapy", Cancer Control, vol. 20, No. 4, pp. 289-297, (Oct. 2013).
Qasim et al., "Molecular remission of infant B-ALL after infusion of universal Talen gene-edited Car T cells", Science Translational Medicine, vol. 9, eaaj2013, pp. 1-8, (Jan. 25, 2017).
Rosenberg et al., "Adoptive cell transfer: a clinical path to effective cancer immunotherapy", Nature Reviews, vol. 8, pp. 299-308, (Apr. 2008).
Rosenberg et al., "Gene Transfer into Humans—Immunotherapy of Patients with Advanced Melanoma, Using Tumor-Infiltrating Lymphocytes Modified by Retroviral Gene Transduction", N. Engl. J. Med., vol. 323, pp. 570-578, (1990).
Rosenberg, "IL-2: The First Effective Immunotherapy for Human Cancer", The Journal of Immunology, vol. 192, No. 12, pp. 5451-5458, (Jun. 6, 2014.
Rosenberg et al., "Prospective Randomized Trial of High-Dose Interleukin-2 Alone or in Conjunction With Lymphokine-Activated Killer Cells for the Treatment of Patients With Advanced Cancer", Journal of the National Cancer Institute, vol. 85, No. 8, pp. 622-632, (Apr. 21, 1993).
Sadelain et al., "The promise and potential pitfalls of chimeric antigen receptors", Current Opinion in Immunology, vol. 21, pp. 215-223, (2009).
Toussaint et al., "Live-attenuated bacteria as a cancer vaccine", Expert Review of Vaccines, vol. 12, No. 10, pp. 1139-1154, (2013).
PCT International Search Report and Written Opinion corresponding to PCT Application No. PCT/US2018/020514, dated Jun. 14, 2018.
PCT International Preliminary Report on Patentability corresponding to PCT Application No. PCTUS2018/020514, dated Sep. 12, 2019.
Extended European Search Report corresponding to European Patent Application No. 18760525.8-1112 dated Oct. 23, 2020.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003—$1^{st}$, (Jan. 2003).
NOF Corporation, PEG Derivatives, Phospholipid and Drug Delivery Materials for Pharmaceuticals, 27 pages, Catalogue 2003—$2^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producerand provider of monodisperse discrete PEG™ (dPEG™) derivatives, (Product Catalog), 26 pages, (Updated: Jul. 18, 2005).
Quanta Biodesign, Ltd., Leading innovator, producerand provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).

\* cited by examiner

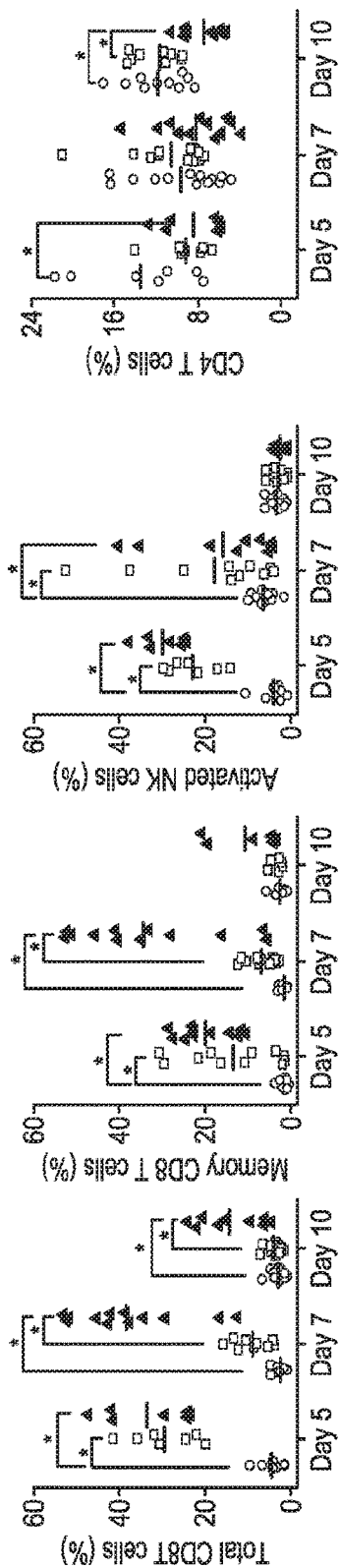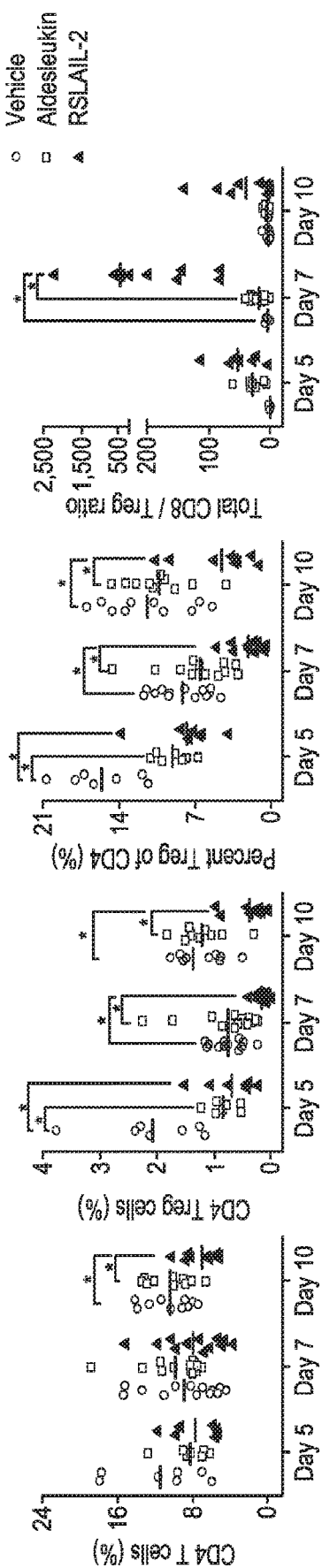

SEQ ID NO:1

| | | | | |
|---|---|---|---|---|
| MYRMQLLSCI | ALSLALVTNS | APTSSSTKKT | QLQLEHLLLD | LQMILNGINN |
| -20 | -10 | 1 | 11 | 21 |
| YKNPKLTRML | TFKFYMPKKA | TELKHLQCLE | EELKPLEEVL | NLAQSKNFHL |
| 31 | 41 | 51 | 61 | 71 |
| RPRDLISNIN | VIVLELKGSE | TTFMCEYADE | TATIVEFLNR | WITFCQSIIS |
| 81 | 91 | 101 | 111 | 121 |

TLT

---

SEQ ID NO:2

APTSSSTKKT QLQLEHLLLD LQMILNGINN

YKNPKLTRML TFKFYMPKKA TELKHLQCLE EELKPLEEVL NLAQSKNFHL

RPRDLISNIN VIVLELKGSE TTFMCEYADE TATIVEFLNR WITFCQSIIS

TLT

---

SEQ ID NO:3

PTSSSTKKT QLQLEHLLLD LQMILNGINN

YKNPKLTRML TFKFYMPKKA TELKHLQCLE EELKPLEEVL NLAQSKNFHL

RPRDLISNIN VIVLELKGSE TTFMCEYADE TATIVEFLNR WITFCQSIIS

TLT

---

SEQ ID NO:4

APTSSSTKKT QLQLEHLLLD LQMILNGINN

YKNPKLTRML TFKFYMPKKA TELKHLQCLE EELKPLEEVL NLAQSKNFHL

RPRDLISNIN VIVLELKGSE TTFMCEYADE TATIVEFLNR WITFCQSIIS

TLT

FIG. 12

SEQUENCE LISTING

```
<160> NUMBER OF SEQ ID NOS: 4

<210> SEQ ID NO 1
<211> LENGTH: 153
<212> TYPE: PRT
<213> ORGANISM: Homo sapiens

<400> SEQUENCE: 1
```

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
145                 150

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 3
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130
```

<210> SEQ ID NO 4
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

IMMUNOTHERAPEUTIC TREATMENT METHOD USING AN INTERLEUKIN-2 RECEPTOR BETA-SELECTIVE AGONIST IN COMBINATION WITH ADOPTIVE CELL TRANSFER THERAPY

CROSS REFERENCE TO RELATED APPLICATIONS

This application is a 35 U.S.C. § 371 application of International Application No. PCT/US2018/020514, filed on Mar. 1, 2018, designating the United States, and claims the benefit of priority under 35 U.S.C. § 119(e) to U.S. Provisional Patent Application No. 62/480,971, filed on Apr. 3, 2017 and to U.S. Provisional Patent Application No. 62/465,506, filed on Mar. 1, 2017, the disclosures of which are incorporated herein by reference in their entireties.

STATEMENT OF GOVERNMENTAL SUPPORT

This invention was made with government support under Grant Nos. CA168585 and CA197633, awarded by the National Institutes of Health. The Government has certain rights in the invention.

REFERENCE TO A SEQUENCE LISTING SUBMITTED VIA EFS-WEB

The instant application contains a Sequence Listing which has been submitted electronically in ASCII format and is hereby incorporated by reference in its entirety. The ASCII text file, created on Aug. 26, 2019, is named SHE0508_00_SL.txt and is 5,696 bytes in size.

FIELD

The instant application relates to (among other things) the field of cancer immunotherapy and involves the treatment of an individual having cancer by providing adoptive cell transfer therapy accompanied by administering to the individual a long-acting IL-2Rβ-biased (i.e., an IL-2Rβ-selective) agonist.

BACKGROUND

New therapies are continually being developed for improved cancer treatment. One of the most promising areas of cancer treatment is immuno-oncology (i.e., cancer immunotherapy). Cancer immunotherapy refers to a diverse set of therapeutic strategies designed to modulate the immune response to induce a patient's own immune system to fight cancer. Among current immunotherapeutic approaches, adoptive cell transfer therapy (also referred to as ACT) has shown promise in treating patients with certain types of cancer. Adoptive cell therapy involves the isolation and ex vivo expansion of tumor specific lymphocytes to yield a greater number of tumor reactive effector T-cells than could be achieved by simple vaccination. The tumor specific T cells are infused into patients with cancer to prime the patients' immune system to kill tumor cells. Adoptive cell transfer has shown effective clinical outcomes, particularly in metastatic melanoma (Dudley, M. E., J. R. Wunderlich, et al., *J Clin Oncol* 23(10): 2346-2357 (2005); Dudley, M. E., J. C. Yang, et al., *J Clin Oncol* 26(32): 5233-5239 (2008)). Adoptive cell transfer can be autologous, as is typical in adoptive T-cell therapies, or can be allogeneic.

Early (first generation) adoptive cell transfer utilized lymphokine-activated killer (LAK) cells with high dose IL-2 for the treatment of patients with advanced cancer, but was shown to not be superior to treatment with IL-2 alone (Rosenberg, S. A., et al., *Journal of the National Cancer Institute*, Vol. 85 (8), 622-632 (1993)). Assays revealed that the expanded LAK cells did not exhibit any anti-tumor activity (Dudley, M. E., et al., *Seminars in Oncology*, Vol 34 (6), 524-531 (2007).

The second generation of adoptive cell transfer employed tumor-infiltrating lymphocytes (TILs) instead of LAK cells. TILs are T cells present within the tumor of a patient that may enhance the ability to specifically recognize tumor antigens to thereby eliminate malignant cells. However, in most cancer patients, the naturally-occurring TILs fail to destroy the tumor, since they are typically either out numbered, not fully activated, or are suppressed. Alternatively, the tumor may have evaded recognition by the immune system, including recognition by TILs. As a result, the main objective of TIL-adoptive cell transfer is to isolate TILs from a patient, followed by ex-vivo stimulation and proliferation to produce large numbers of activated tumor-specific T-cells. The expanded TILs are then infused back into the patient. In an initial TIL-ACT trial for metastatic melanoma, patients were treated with autologous TILs accompanied by high dose intravenous IL-2 as a stimulating growth factor for the TILs. The pleiotropic nature of IL-2 as well as its short half-life, allows for growth of both regulatory as well as effector T cells of limited in vivo persistence. Response rates were low, and the persistence of TILs in the circulation was barely 0.1 percent one week after administration (Rosenberg, S. A., et al., *New England Journal of Medicine*, Vol. 323 (9), 570-578 (1990)). Poor persistence of effector T cells and stimulation of regulatory TILs may have contributed to the lack of response.

The above-described trials indicated the need to improve anti-tumor responses. The next generation of adoptive cell transfer studies included the addition of lymphodepleting preconditioning of the patient with a goal of suppressing endogenous regulatory T-cells and to provide an optimal environment for the infused TILs. However, these later studies demonstrated associated patient toxicities including hypotension, pulmonary congestion, vascular leak syndrome, and bone marrow suppression (Dudley, M. E., et al., *Journal of Clinical Oncology*, Vol. 23 (10), 2346-2357 (2005). In addition to the foregoing, another drawback of this approach was the extremely high dropout rate of patients, primarily due to the aforementioned toxicities and lack of response. Additionally, the population of T cells that were expanded remained in question as both regulatory and effector cells could be indiscriminately expanded. Finally, the lack of persistence of the transferred cells in the body remains a major issue.

Despite the challenges noted above among others, adoptive cell transfer clinical trials for treating cancer continue to enroll patients, since in advanced metastatic cancer, few therapies are effective, including checkpoint inhibitor antibodies. Ongoing adoptive cell transfer trials include various types of cell expansion agents, transferred cells, patient conditioning, oncolytic agents; one approach for improving adoptive cell transfer involves the transfer of genetically modified peripheral T-cells instead of TIL. The TIL protocol typically requires that a patient undergo surgery in order to resect tumor tissues for TIL isolation; in contrast, T-cell adoptive cell therapy typically allows the patient to circumvent surgery and only requires patient leukopheresis to obtain peripheral T cells for genetic modification. This approach requires prior knowledge of what tumor antigens may be present. In addition, to date, genetically engineered T cell therapy (CAR-T or TCR) has only been effective for liquid tumors and not solid tumors, and the question of T cell subset population remains. Solid tumors have only responded to TILs and interleukin-2. Even with these approaches, the population of cells expanded by interleukin-2 is unclear, as the expanded cell population may comprise regulatory, helper and effector T cells. This arises from the pleiotropic nature of naturally-occurring interleukin-2, which can equally expand regulatory and effector T cells.

Although there have been substantial efforts in developing effective adoptive cell transfer therapies encompassing various platforms to date, there remains a need to provide new and more effective immunotherapeutic adoptive cell transfer strategies and related treatment regimens that overcome one or more of the disadvantages of current therapies to harness the potential of this immuno-cell therapy based approach. Thus, the present disclosure seeks to address this and other needs by providing new and efficient cancer immunotherapies utilizing adoptive cell transfer that enable skewing the expanded T cell population towards a tumor-killing phenotype with greater persistence.

SUMMARY

In a first aspect, provided herein is a method comprising adoptive cell transfer to a subject having cancer in combination with the administration of an IL-2Rβ-activating amount of a long-acting IL-2Rβ-biased agonist, to be described in greater detail below. In one or more embodiments, the long-acting IL-2Rβ-biased agonist is effective to preferentially expand effector T cells. The present disclosure arises at least in part from the recognition that a combination treatment regimen including one or more cycles and/or doses of adoptive cell therapy and a long acting, biased IL-2Rβ-activating agonist of effector T-cells, administered either sequentially, in either order, or substantially simultaneously, can be particularly effective in treating cancer in some subjects and/or can initiate, enable, increase, enhance or prolong the activity and/or number of immune cells, or result in a beneficial response against cancer cells (e.g., stabilization, regression, shrinkage, necrosis, etc., as applicable), including liquid and solid cancers, to an extent that is enhanced over either single immunotherapeutic approach alone.

In a second aspect, provided herein is a combination therapy for the treatment of cancer comprising adoptive cell therapy and a long-acting IL-2Rβ-biased agonist.

In a third aspect, provided is a method of enhancing the therapeutic effectiveness of adoptive cell therapy, the method comprising providing adoptive cell therapy to a subject having cancer, and administering to the subject an IL-2Rβ-activating amount of a long-acting IL-2Rβ-biased agonist, wherein the long-acting IL-2Rβ-biased agonist is effective to improve the subject's response to the adoptive cell therapy.

In yet a fourth aspect, provided is a method of inhibiting accumulation of regulatory T cells (Tregs) in a subject undergoing treatment for cancer, comprising infusing into the subject cells T-cells (e.g., that have been harvested from the subject's blood or tumor, and expanded in vitro), and administering to the subject an IL-2Rβ-activating amount of a long acting IL-2Rβ-biased agonist. The long acting IL-2Rβ-biased agonist is administered in an amount effective to treat a cancerous tumor, where when evaluated, for example, in a mouse or other suitable in vivo model of cancer, the treatment is effective to inhibit accumulation of regulatory T cells selected from the group consisting of CD4+ Tregs, CD25+ Tregs, and FoxP3+ Tregs in the tumor by an amount that is enhanced over that observed upon administration of a non-long acting version of the IL-2R agonist combined with adoptive cell transfer, or over that observed upon treatment with either single immuno-oncological treatment alone (i.e., administration of the long acting IL-2Rβ-biased agonist or adoptive cell transfer alone).

By way of clarity, with regard to the sequence of administering, wherein the term "administering" is used in this instance to refer to delivery of either the adoptive cells or the long acting IL-2Rβ-biased agonist, the adoptive cells and the long acting IL-2Rβ-biased agonist may be administered concurrently or sequentially and in any order. Moreover, treatment may comprise a single cycle of therapy, or may comprise multiple cycles. Following an initial cycle of therapy comprising adoptive cell transfer and administration of the long acting IL-2Rβ-biased agonist, additional rounds of therapy may include adoptive cell transfer in combination with administration of the long acting IL-2Rβ-biased agonist, or adoptive cell therapy that is not accompanied by administration of the long acting IL-2Rβ-biased agonist, or administration of the long acting IL-2Rβ-biased agonist that is not accompanied by adoptive cell transfer.

The following embodiments are meant to apply equally to each of the aspects described above, and to be considered both singly and in combination as applicable, unless indicated otherwise.

In one or more embodiments, the subject is a human subject.

In one or more additional embodiments, the cancer is a solid cancer. For example, the cancer is, in one or more embodiments, selected from the group consisting of breast cancer, ovarian cancer, colon cancer, prostate cancer, bone cancer, colorectal cancer, gastric cancer, malignant melanoma, liver cancer, small cell lung cancer, non-small cell lung cancer, pancreatic cancer, thyroid cancers, kidney cancer, cancer of the bile duct, brain cancer, cervical cancer, maxillary sinus cancer, bladder cancer, esophageal cancer, and adrenocortical cancer.

In yet one or more further embodiments, the cancer is selected from melanoma, kidney, non-small cell lung, breast, bladder, head and neck, and colon cancer.

In one or more particular embodiments, the breast cancer is triple negative breast cancer.

In one or more embodiments, when treating a solid cancerous tumor, the method is effective to result in a reduction in solid tumor size of at least about 25% when evaluated after a single cycle of treatment.

In some additional embodiments, the cancer is metastatic.

In some further embodiments, the cancer is a liquid cancer such as a blood cancer. In some embodiments, the cancer is lymphoma or leukemia. In one or more related embodiments, the cancer is leukemia selected from Hodgkin and non-Hodgkin lymphoma.

In one or more embodiments, the adoptive cell therapy comprises infusion of adoptive T cells or NK cells.

In one or more additional embodiments, the adoptive cell therapy comprises infusion of tumor-infiltrating lymphocytes (TIL).

In one or more embodiments, the cells are autologous cells.

In one or more additional embodiments, the cells are allogeneic cells. In some embodiments, the allogeneic cells are targeted against tumor antigens.

In one or more additional embodiments, the cells are genetically engineered.

In some embodiments, adoptive cell therapy is provided prior to administration of an IL-2Rβ-activating amount of a long acting IL-2Rβ-biased agonist.

In some embodiments, the long acting IL-2Rβ-biased agonist comprises aldesleukin releasably covalently attached to polyethylene glycol. In yet some additional embodiments, the long acting IL-2Rβ-biased agonist comprises interleukin-2, such as, for example, aldesleukin, releasably covalently attached to from 4, 5, and 6, or to from 4, 5, 6, and 7 polyethylene glycol polymers. In yet some further embodiments, the long acting IL-2Rβ-biased agonist comprises aldesleukin releasably covalently attached to an average of about 6 polyethylene glycol polymers. In one or more additional embodiments, the polyethylene glycol polymers that are releasably covalently attached to aldesleukin are branched polymers.

In some embodiments, adoptive cell therapy is administered once (in a single round of treatment), with administration of a long acting IL-2Rβ-biased agonist, followed by additional rounds of administration of the long acting IL-2Rβ-biased agonist.

In one or more embodiments directed to the long acting IL-2Rβ-biased agonist, the long acting IL-2Rβ-biased agonist is comprised in a composition further comprising a pharmaceutically acceptable excipient.

Additional aspects and embodiments are set forth in the following description and claims.

BRIEF DESCRIPTION OF THE DRAWINGS

FIGS. 1A-1H. These figures illustrate immune cell alterations in B16F10 mouse melanoma models following treatment with a single dose of an exemplary long acting IL-2Rβ-biased agonist, RSLAIL-2 (described below, where "RSLAIL-2" refers to a releasably PEGylated interleukin-2 molecule), or 5 daily doses of aldesleukin as described in detail in Example 2. Tumor-infiltrating lymphocytes (TILs) were isolated from animals at the time points indicated and immune cell populations were assessed by flow cytometry. Each data point represents an individual mouse tumor and the line represents the mean. Data were combined from 2 to 4 independent studies with 3 to 4 replicates at each time point. FIG. 1A shows total percentage of CD8 T cells in the tumor at various time points (days 5, 7, and 10) following treatment with each of vehicle (open circles), aldesleukin (filled squares) and RSLAIL-2 (filled triangles); FIG. 1B shows percentage of memory CD8 T cells in the tumor at various time points following treatment with each of vehicle (open circles), aldesleukin (filled squares) and RSLAIL-2 (filled triangles); FIG. 1C shows percentage of activated NK cells in the tumor at various time points (days 5, 7, and 10) following treatment with each of vehicle (open circles), aldesleukin (filled squares) and RSLAIL-2 (filled triangles); FIGS. 1D and 1E show percentage of CD4 T cells in the tumor at various time points (days 5, 7, and 10) following treatment; FIG. 1F shows percentage of CD4 Treg cells in the tumor at various time points (days 5, 7, and 10) following treatment; FIG. 1G shows percentage of Treg cells of total CD4 cells following treatment; and FIG. 1H provides the ratio of total CD8 cells to Treg cells following treatment.

FIG. 6A and FIG. 6B: Top plot, solid triangles: ACT+ RSLAIL-2 as indicated; middle plot, solid squares: ACT+ IL-2; bottom plot, solid circles: ACT+vehicle. These images demonstrate the effectiveness of an adoptive cell transfer therapy in combination with administration of an agent such as RSLAIL-2 rather than with the interleukin-2, aldesleukin, since a persistent response was observed with the ACT/RSLAIL-2 combination therapy, as opposed to the ACT/IL-2 therapy where the response waned, even with multiple treatments of IL-2 (aldesleukin).

FIG. 7A illustrates the number of Thy 1.1 CD8 cells in the tumor for each of the treatment groups (progressing from left to right per bar, ACT+vehicle; ACT+IL-2 and ACT+ RSLAIL-2). FIG. 7B illustrates the number of CD4 T regs in the tumor for each of the treatment groups (progressing from left to right per bar, ACT+vehicle; ACT+IL-2 and ACT+RSLAIL-2). FIG. 7C provides a ratio of the number of CD8 cells to Tregs in the tumor for each of the treatment groups as described above. These data illustrate a CD8/Treg cell ratio in the tumor that is greater than that observed in the spleen for the ACT+RSLAIL-2 combination, suggesting that normal tissue is not significantly impacted. Morever, for the ACT+RSLAIL-2 combination, the CD8/Treg ratio is substantially higher than that achieved in the ACT+IL-2 combination, and with fewer administrations of RSLAIL-2.

FIG. 8A illustrates the number of Thy 1.1 CD8 cells in the spleen for each of the treatment groups (progressing from left to right per bar, ACT+vehicle; ACT+IL-2 and ACT+RSLAIL-2). FIG. 8B illustrates the number of CD4 T regs in the spleen for each of the treatment groups (progressing from left to right per bar, ACT+vehicle; ACT+IL-2 and ACT+RSLAIL-2). FIG. 8C provides a ratio of the number of CD8 cells to Tregs in the spleen for each of the treatment groups as described above.

FIG. 12 provides exemplary interleukin-2 sequences for use in preparing a long acting IL-2Rβ-biased agonist.

DETAILED DESCRIPTION

Figure 2:
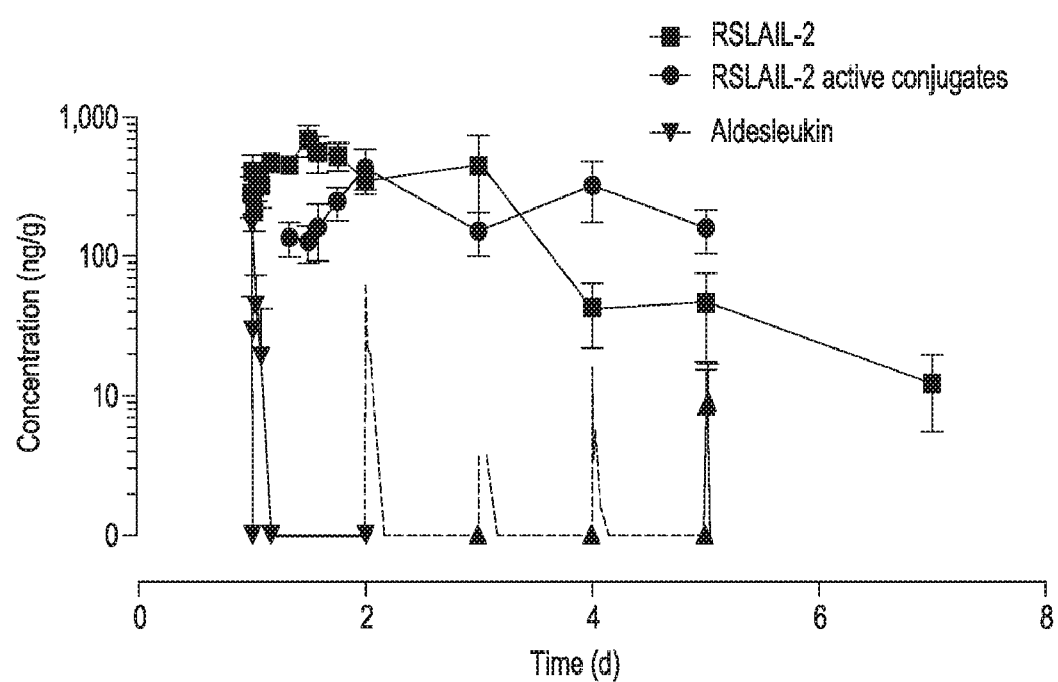
FIG. 2 is a graph demonstrating tumor pharmacokinetics of RSLAIL-2 (closed squares) (and its released active conjugated-IL-2 forms, closed circles) in comparison to unmodified IL-1 (aldesleukin, closed upside down triangles) as described in Example 3.

As used in this specification, the singular forms "a," "an," and "the" include plural referents unless the context clearly dictates otherwise.

In describing and claiming certain features of this disclosure, the following terminology will be used in accordance with the definitions described below unless indicated otherwise.

"Water soluble, non-peptidic polymer" refers to a polymer that is at least 35% (by weight) soluble in water at room temperature. Preferred water soluble, non-peptidic polymers are however preferably greater than 70% (by weight), and more preferably greater than 95% (by weight) soluble in water. Typically, an unfiltered aqueous preparation of a "water-soluble" polymer transmits at least 75% of the amount of light transmitted by the same solution after filtering. Preferably, such unfiltered aqueous preparation transmits at least 95% of the amount of light transmitted by the same solution after filtering. Most preferred are water-soluble polymers that are at least 95% (by weight) soluble in water or completely soluble in water. With respect to being "non-peptidic," a polymer is non-peptidic when it contains less than 35% (by weight) of amino acid residues.

The terms "monomer," "monomeric subunit" and "monomeric unit" are used interchangeably herein and refer to one of the basic structural repeat units of a polymer. In the case of a homo-polymer, a single repeating structural unit forms the polymer. In the case of a co-polymer, two or more structural units are repeated—either in a pattern or randomly—to form the polymer. Preferred polymers used in connection with the present disclosure are homopolymers. The water-soluble, non-peptidic polymer comprises one or more monomers serially attached to form a chain of monomers.

"PEG" or "polyethylene glycol," as used herein, is meant to encompass any water-soluble poly(ethylene oxide). Unless otherwise indicated, a "PEG polymer" or a polyethylene glycol is one in which substantially all (preferably all) monomeric subunits are ethylene oxide subunits, though, the polymer may contain distinct end capping moieties or functional groups, e.g., for conjugation. PEG polymers for use in the present disclosure will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. As stated above, for the PEG polymers, the variable (n) typically ranges from about 3 to 4000, and the terminal groups and architecture of the overall PEG can vary.

"Branched," in reference to the geometry or overall structure of a polymer, refers to a polymer having two or more polymer "arms" or "chains" extending from a branch point or central structural feature.

A "physiologically cleavable" or "hydrolyzable" or "degradable" bond is a relatively labile bond that typically reacts with water (i.e., is hydrolyzed) under physiological conditions and under any suitable method of hydrolysis. The tendency of a bond to hydrolyze in water may depend not only on the general type of linkage connecting two atoms within a given molecule but also on the substituents attached to these atoms and the overall structure of the molecule. Hydrolytically unstable or weak linkages may typically include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages generally include but are not limited to the following: carbon-carbon bonds (e.g., in aliphatic chains), ethers, amides, amines, and the like. Generally, a stable linkage is one that exhibits a rate of hydrolysis of less than about 1-2% per day under physiological conditions. Hydrolysis rates of representative chemical bonds can be found in most standard chemistry textbooks.

A covalent "releasable" linkage, for example, in the context of a polyethylene glycol moiety that is covalently releasably attached to an active moiety such as interleukin-2, is one which releases or detaches a polyethylene glycol moiety from the active moiety (i.e., dePEGylation) by any suitable mechanism.

As used herein, the term "treating cancer" is not intended to be an absolute term, and may include, for example, reducing the size of a tumor or number of cancer cells, causing a cancer to go into remission, or preventing growth in size or cell number of cancer cells, and the like. In some circumstances, treatment in accordance with the instant disclosure leads to an improved prognosis.

As used herein, the phrase "a subject in need of treatment" refers to an individual or subject that has been diagnosed with cancer.

As used herein, the term "enhancing", for example, in the context of an enhanced response, refers to a subject's or tumor cell's improved ability to respond to treatment, e.g., as disclosed herein, when compared to given baseline. For example, an enhanced response may comprise an increase in responsiveness of at least 5%, 10%, 15%, 20%, 25%, 30%, 35%, 40%, 45%, 50%, 55%, 60%, 65%, 70%, 75%, 80%, 85%, 90%, 95% or 98% or more, based upon any one or more indicators of responsiveness to treatment. As used herein, "enhancing" can also refer to enhancing the number of subjects who favorably respond to treatment, e.g., when compared to a given basis for such comparison.

The phrases "therapeutically effective", "therapeutically effective amount", "effective amount" or "in an amount effective" refer to a sufficient amount or dosage to promote the desired physiological response, such as but not limited to an amount or dosage sufficient to promote a T-cell response.

"Substantially" or "essentially" means nearly totally or completely, for instance, 95% or greater of a given quantity.

"Pharmaceutically acceptable excipient" or "pharmaceutically acceptable carrier" refers to a component that may be included in the compositions described herein and causes no significant adverse toxicological effects to a subject.

The term "patient," or "subject" as used herein refers to a living organism suffering from or prone to a condition that can be prevented or treated by administration of a compound or composition or combination as provided herein, such as a cancer, and includes both humans and animals. Subjects include, but are not limited to, mammals (e.g., murines, simians, equines, bovines, porcines, canines, felines, and the like), and preferably are human.

Overview

Although a promising therapy for inducing an effective anti-tumor response, following adoptive cell therapy, cancerous tumors frequently relapse after an initial response. Moreover, current protocols for adoptive T cell transfer generally require an immune stimulant such as a cytokine or other agent to stimulate and maintain T-cell proliferation, although such stimulating agents may stimulate both effector and regulatory T-cells. In an effort to address at least some of the shortcomings associated with current adoptive cell transfer strategies, provided herein is a method comprising administering to a subject having cancer, ex-vivo expanded tumor reactive T-cells and an IL-2Rβ-activating amount of a long acting IL-2Rβ-biased agonist. While cytokines such as high dose IL-2 have long been used in combination with adoptive cell transfer, such treatment has resulted in reported patient toxicities such as capillary leak syndrome, lack of persistence of infused cells, and low response rates. Moreover, clinically approved IL-2 expands both tumor-killing CD8+ effector T cells (CD8T) as well as regulatory T cells (Tregs) through binding the IL-2Rβγ and IL-2Rαβγ complexes, respectively, such that Tregs in the tumor can lead to immune suppression that hampers the desired anti-tumor response. Thus, in light of these and other disadvantages, further enhancements are needed to provide durable, reproducible and effective adoptive cell transfer-based cancer therapies having improved anti-tumor specificities. Thus, the present disclosure is based, at least in part, on the discovery of a particularly beneficial therapeutic combination comprising cell-based therapy and administration of a long-acting IL-2R agonist, and more specifically, an IL-2Rβ-biased agonist, as illustrated in exemplary in-vivo animal models.

Il-2 stimulates immune cell proliferation and activation through a receptor-signalling complex containing alpha (IL2Rα, CD25), beta (IL2Rβ, CD122) and common gamma chain receptors ($γ_c$, CD132). At high doses, IL-2 binds to the heterodimeric IL2Rβγ receptor leading to desired expansion of tumor killing CD8+ memory effector T (CD8 T) cells. However, IL2 also binds to its heterotrimeric receptor IL2Rαβγ with greater affinity, which expands immuosuppressive CD4+, CD25+ regulatory T cells (Tregs), which may lead to an undesirable effect for cancer immunotherapy. Thus, in an effort to overcome one or more drawbacks associated with IL-2-enhanced immuno-oncology strategies, provided herein is a treatment modality that combines adoptive cell transfer with administration of an IL-2Rβ-biased agonist, and in particular, a long-acting IL-2Rβ-biased agonist. Without being bound by theory, the Applicants have discovered that by utilizing a long-acting interleukin-2 molecule in which a region that interacts with the IL-2Rα subunit responsible for activating immunosuppressive Tregs is masked (i.e., its activity suppressed or dampened), i.e., a long acting IL-2Rβ-biased agonist, one can, among other things, selectively expand adoptive cell transfer-induced T-cell responses to achieve superior therapeutic efficacy, as will become apparent from the instant disclosure and supporting examples.

Adoptive Cell Transfer Therapy

The treatment methods provided herein comprise administering ex vivo expanded tumor reactive T cells, i.e., for stimulating a cancer specific-immune response. The compositions and methods provided herein find use in, among other things, both clinical and research applications. Various adoptive cell transfer therapies can be administered in accordance with the methods described herein, and the disclosure is not limited in this regard. Without being bound by theory, it is believed that enhanced anti-tumor outcomes can be achieved via the IL-2 pathway (i.e., via administration, along with adoptive cell transfer, of a long-acting IL-2Rβ-biased agonist) to simulate the desired T-cell response due to the complementary mechanisms of immune activation of adoptive cell transfer, e.g., T-cell transfer, and a long-acting IL-2Rβ-biased agonist as provided herein.

Any suitable adoptive cell transfer therapy can be used in the methods provided herein, and the disclosure is not limited in this regard. See for example, Rosenberg, S., et al., *Adoptive Cell Transfer: A clinical path to effective cancer immunotherapy. Nat Rev Cancer.* 2008 April; 8(4): 299-308. For example, adoptive T cell or NK cell therapy can be used. For instance, following selection, tumor-specific host T cells may be combined ex vivo with tumor antigens or cells, expanded, and reinfused into the subject. Prior to infusion, patient pre-conditioning may also be carried out, for example, using lymphodepleting nonmyeloablative chemotherapy (NMC) to suppress endogenous regulatory T-cells and to provide an optimized environment for the infused T-cells; alternatively, cyclophosphamide or any other suitable conditioning agent may be used. Such pre-conditioning is for eliminating or substantially reducing numbers of Tregs (regulatory T cells) and lymptocytes, which compete with the transferred cells for homeostatic cytokines. The host cells may be isolated from a variety of sources, such as lymph nodes, e.g. inguinal, mesenteric, superficial distal auxiliary, etc.; bone marrow; spleen; or peripheral blood, as well as from the tumor, e.g. tumor infiltrating lymphocytes. The cells may be allogeneic or, preferably, autologous. For ex vivo stimulation, the host cells are aseptically removed, and are suspended in any suitable media, as known in the art. The cells are stimulated and expanded using any of a variety of protocols, particularly combinations of anti-CD3, B7, anti-CD28, etc. Suitable protocols for ex-vivo expansion of host T cells are described in "*Focus on Adoptive T Cell Transfer Trials in Melanoma*", Clinical and Developmental Immunology, Vol 2010, Art. ID 260267.

For example, adoptive cell transfer may be carried out by (i) obtaining autologous lymphocytes from a mammalian subject such as a human, (ii) culturing the autologous lymphocytes to produce expanded lymphocytes, and (ii) administering the expanded lymphocytes to the subject (i.e., patient). Preferably, the lymphocytes are tumor-derived, e.g., they are TILs, and are isolated from a subject to be treated (i.e. autologous transfer). Autologous adoptive cell therapy may also be performed by (i) culturing autologous lymphocytes to produce expanded lymphocytes; (ii) administering nonmyeloablative lymphodepleting chemotherapy (NMC) to the subject; and (iii) after administering NMC, administering the expanded lymphocytes. Autologous TILs may be obtained, e.g., from the stroma of resected tumors, for example, by mechanically disaggregating the tumor or enzymatically (e.g., using collagenase or DNase). Alternatively, the cells can be derived from blood, e.g., if they are genetically engineered to express antitumor T-cell receptors (TCRs) or chimeric antigen receptors (CARs) enriched with mixed lymphocyte tumor cell cultures or cloned using autologous antigen presenting cells and tumor-derived peptides.

Expansion of lymphocytes, including tumor-infiltrating lymphocytes, such as T cells, can be accomplished by any of a number of methods as are known in the art. For example, T cells can be expanded using non-specific T-cell receptor stimulation in the presence of feeder lymphocytes and interleukin-2 (IL-2), IL-7, IL-15, IL-21, or combinations thereof. The non-specific T-cell receptor stimulus can include, for example, a stimulating amount of a mouse monoclonal anti-CD3 antibody (available, e.g., from LS Bio, Seattle Wash.). Alternatively, T cells can be rapidly expanded by stimulation of peripheral blood mononuclear cells (PBMC) in vitro with one or more antigens (including antigenic portions thereof, such as epitopes), which can be optionally expressed from a vector, such as an human leukocyte antigen A2 (HLA-A2) binding peptide, in the presence of a T-cell growth factor, such as interleukin-2 or interleukin-15, with interleukin-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated autologous lymphocytes or with irradiated HLA-A2+ allogeneic lymphocytes and interleukin-2.

Specific tumor reactivity of the expanded TILs can be tested by any method known in the art, e.g., by measuring cytokine release (e.g., interferon-gamma) following co-culture with tumor cells. For example, the adoptive cell transfer may include enriching cultured TILs for CD8+ T cells prior to rapid expansion of the cells. Following culture of the TILs in a medium containing interleukin-2, the T cells are depleted of CD4+ cells and enriched for CD8+ cells using, for example, a CD8 microbead separation. In some embodiments, a T-cell growth factor that promotes the growth and activation of the autologous T cells is administered to the subject either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, IL-12 and IL-21, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Adopted cell therapy may also be carried out using genetically modified peripheral T cells, i.e., tumor-targeted T cells formed by genetic transfer of antigen-specific receptors which typically consist of either MHC-restricted T cell receptors (TCR) or non-MHC-restricted synthetic chimeric antigen receptors (see, e.g., Sadelain, M., et al, *Current Opinion in Immunology*, Vol 21 (2), 215-223 (2009); see also Kalos, M., et al., *Sci Transl Med* 2011; 3: 95ra73; and Grupp S A, et al, *N Engl J Med* 2013; 368: 1509-1518). Using this approach, highly avid anti-tumor T cells are identified and the genes encoding their T-cell receptors (TCRs) are cloned and inserted into retroviruses. Retroviral supernatants are then produced and used to insert the T-cell receptors into normal lymphocytes. Expression of the T-cell receptor is then compared in untransduced (UnTd) and transduced (Td) cells by fluorescence-activated cell sorting analysis and by recognition in vitro of HLA-A2$^+$ 526 melanoma line and not the HLA-A2$^-$ 888 melanoma line (Rosenberg, S., et al., *Nat Rev. Cancer,* 2008 April; 84(4): 299-308). Universal type T cells can also be used such as described by Qasim, W., et al., *Sci. Transl. Med.* 9, eaaj2013 (2017). For example, universal CAR19 T cells can be generated using TALEN-mediated cell engineering in combination with lentiviral transduction and used in adopted cell therapy. The cells are generated by lentiviral transduction of non-human leukocyte antigen-matched donor cells and simultaneous transcription activator-like effector nuclease (TALEN)-mediated gene editing of T cell receptor a chain and CD52 gene loci.

The expanded cells are then administered to the host by infusion, e.g., intravenous or intra-arteria infusion or other suitable form of delivery, which typically lasts from about 30 to about 60 minutes, although shorter or longer durations may be needed. For example, from about $1 \times 10^{10}$ lympocytes to about $15 \times 10^{10}$ lymphocytes are typically administered. Other routes of administration include intraperitoneal, intrathecal, and intralymphatic. The expanded cells are provided in a suitable medium that may optionally include any of a variety of pharmaceutically acceptable additives, binders, fillers, carriers, preservatives, stabilizing agents, emulsifiers, buffers, and the like. Diluents and excipients include water, saline, and glucose. Representative media include but are not limited to, for example, Multiple Electrolytes Injection, Type 1, USP having a nominal pH range of about 5.5 to 8.0; tissue culture media containing human serum or fetal bovine serum; or a xeno-free and serum-free medium such as, for example, PRIME-XV T Cell Expansion XSFM (Irvine Scientific). Commercially available media include RPMI 1640 (Thermo Fisher Scientific, Waltham, Mass.), AIM V cell culture medium (Thermo Fisher Scientific, Waltham Mass.), and X-VIVO 15 (Lonza, Basel, Switzerland).

Long Acting, IL-2Rβ-Biased Agonist

The methods described herein involve the administration of a long acting, IL-2Rβ-biased agonist. In this regard, the disclosure is not limited to any particular long acting, IL-2Rβ-biased agonist so long as the agonist exhibits an in vitro binding affinity for IL-2Rβ that is at least 5 times greater (more preferably at least 10 times greater) than the binding affinity for IL-2Rαβ in the same in vitro model, and has at least an effective 10-fold in vivo half-life greater than the unmodified IL-2 (half-life based on the in-vivo disappearance of IL-2). By way of example, it is possible to measure binding affinities against IL-2 as a standard. In this regard, the RSLAIL-2 molecule referenced in Example 1 and described below exhibits about a 60-fold decrease in affinity to IL-2Rαβ relative to IL-2, but only about a 5-fold decrease in affinity to IL-2Rβ relative to IL-2. Thus, an exemplary long acting, IL-2Rβ-biased agonist is RSLAIL-2.

Non-limiting examples of long acting, IL-2Rβ-biased agonists are described in International Patent Publication Nos. WO 2012/065086 and in WO 2015/125159. An exemplary long acting, IL-2Rβ-biased agonist is RSLAIL-2 referenced in Example 1 in the present application, where the releasable PEG is based upon a 2,7,9-substituted fluorene as shown below with poly(ethylene glycol) chains extending from the 2- and 7-positions of a central fluorene ring via amide linkages (fluorene-C(O)—NH~) to provide a branched PEG. The fluorenyl-based branched PEG moieties are releasably covalently attached to amino groups of the interleukin-2 moiety. The linkage between IL-2 moiety amino groups and the fluorenyl-based branched PEG moiety is a carbamate linkage attached via a methylene group (—CH$_2$—) to the 9-position of the fluorene ring. Releasable PEGs having this general structure typically undergo a β-elimination reaction under physiological conditions to slowly release the PEG moieties that are covalently attached to IL-2. It is believed that the PEG moieties release sequentially following administration.

In this regard, in some preferred embodiments, the long acting, IL-2Rβ-biased agonist comprises compounds encompassed by the following formula, Formula I:

wherein IL-2 is interleukin-2 and each "n" is an integer from about 3 to about 4000, or pharmaceutically acceptable salts thereof. Representative ranges for each "n" (that is, each PEG "arm"), include, for example, an integer from about 40 to about 550, or an integer from about 60 to about 500, or an integer from about 113 to about 400. In a preferred embodiment, "n" in each of the linear PEG arms shown about is about 227.

In one or more embodiments, the long acting IL-2Rβ-biased agonist having a formula as set forth in the preceding paragraph is comprised in a composition comprising the composition contains no more than 10% (based on a molar amount), and preferably no more than 5% (based on a molar amount), of compounds encompassed by the following formula, Formula II:

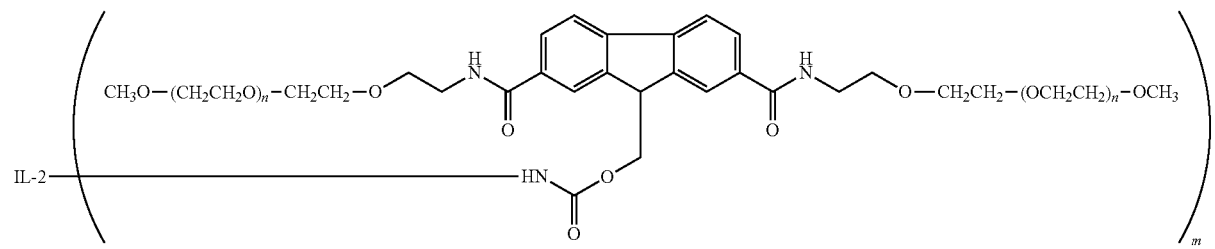

wherein IL-2 is interleukin-2, "m" (referring to the number of polyethylene glycol moieties attached to IL-2) is an integer selected from the group consisting of 1, 2, 3, 7 and >7, or pharmaceutically acceptable salts thereof.

In some embodiments, e.g., in reference to Formula I, the long acting IL-2Rβ-biased agonist possesses on average about six branched polyethylene glycol moieties releasably attached to IL-2. In some further embodiments, e.g., in reference to Formula I, the long acting IL-2Rβ-biased agonist is generally considered to be an inactive prodrug, i.e., that is inactive upon administration, and by virtue of slow release of the polyethylene glycol moieties in vivo, provides active conjugated forms of interleukin-2 having fewer PEG moieties attached than in the conjugate that is initially administered, and effective to achieve sustained concentrations at a tumor site.

Additional exemplary compositions of RSLAIL-2 comprise compounds in accordance with the above formula wherein the overall polymer portion of the molecule has a weight average molecular weight in a range of from about 250 Daltons to about 90,000 Daltons. Additional suitable ranges include weight average molecular weights in a range selected from about 1,000 Daltons to about 60,000 Daltons,

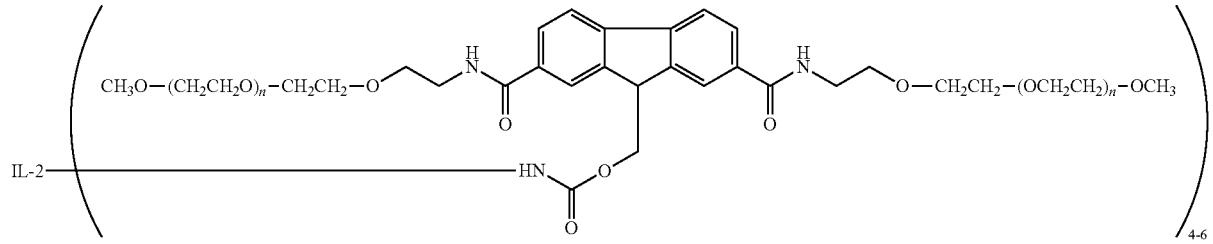

in a range of from about 5,000 Daltons to about 60,000 Daltons, in a range of about 10,000 Daltons to about 55,000 Daltons, in a range of from about 15,000 Daltons to about 50,000 Daltons, and in a range of from about 20,000 Daltons to about 50,000 Daltons.

Additional illustrative weight-average molecular weights for the polyethylene glycol polymer portion include about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. In some embodiments, the weight-average molecular weight of the polyethylene glycol polymer is about 20,000 daltons.

As described above, the long-acting, IL-2Rβ-biased agonist may be in the form of a pharmaceutically-acceptable salt. Typically, such salts are formed by reaction with a pharmaceutically-acceptable acid or an acid equivalent. The term "pharmaceutically-acceptable salt" in this respect, will generally refer to the relatively non-toxic, inorganic and organic acid addition salts. These salts can be prepared in situ in the administration vehicle or the dosage form manufacturing process, or by separately reacting a long-acting interleukin-2 as described herein with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, oxylate, mesylate, glucoheptonate, lactobionate, and laurylsulphonate salts and the like. (See, for example, Berge et al. (1977) "Pharmaceutical Salts", J. Pharm. Sci. 66:1-19). Thus, salts as described may be derived from inorganic acids such as hydrochloride, hydrobromic, sulfuric, sulfamic, phosphoric, nitric, and the like; or prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In reference to the foregoing IL-2Rβ-biased agonist, the term "IL-2" as used herein refers to a moiety having human IL-2 activity. The term, 'residue', in the context of residue of IL-2, refers to the portion of the IL-2 molecule that remains following covalent attachment to a polymer such as a polyethylene glycol, at one or more covalent attachment sites, as shown in the formula above. It will be understood that when the unmodified IL-2 is covalently attached to a polymer such as polyethylene glycol, the IL-2 becomes slightly altered due to the presence of one or more covalent bonds associated with linkage to the polymer(s). This slightly altered form of the IL-2 attached to another molecule such as a polyethylene glycol moiety may be referred to herein in some instances as a "residue" of IL-2, although it is to be understood that in reference to a polyethylene glycol conjugate of IL-2, reference to IL-2 in such conjugate encompasses such slightly altered forms of IL-2 in which, for example, amino groups within the IL-2 molecule (e.g., lysines) are covalently attached to one or more PEG moieties.

For example, proteins having an amino acid sequence corresponding to any one of SEQ ID NOs: 1 through 4 described in International Patent Publication No. WO 2012/065086 are considered to be exemplary IL-2 proteins, as are any proteins or polypeptides substantially homologous thereto. These illustrative interleukin-2 sequences are also provided herein and include the following: human interleukin-2 including a signal peptide sequence, human interleukin-2, aldesleukin, and an interleukin-2 specific agonist (also referred to as BAY 50-4798). The term, "substantially homologous", means that a particular subject sequence, for example, a mutant sequence, varies from a reference sequence by one or more substitutions, deletions, or additions, the net effect of which does not result in an adverse functional dissimilarity between the reference and subject sequences. For the purposes herein, sequences having greater than 95 percent homology, equivalent biological activity (although not necessarily equivalent strength of biological activity), and equivalent expression characteristics are considered substantially homologous. For purposes of determining homology, truncation of the mature sequence should be disregarded. As used herein, the term "IL-2" includes such proteins modified deliberately, as for example, by site directed mutagenesis or accidentally through mutations. These terms also include analogs having from 1 to 6 additional glycosylation sites, analogs having at least one additional amino acid at the carboxy terminal end of the protein wherein the additional amino acid(s) includes at least one glycosylation site, and analogs having an amino acid sequence which includes at least one glycosylation site. The term includes both natural and recombinantly produced moieties. In addition, the IL-2 can be derived from human sources, animal sources, and plant sources. One exemplary and preferred interleukin-2 is recombinant IL-2 referred to as aldesleukin. Aldesleukin (SEQ ID NO:3) differs from native IL-2 in that it is not glycosylated since it is derived from E. coli, has no N-terminal alanine, and possesses a serine substituted for cysteine at amino acid position 125.

Conventional approaches, such as those involving radiolabeling a compound, administering it in vivo, and determining its clearance, can be used to determine whether a compound proposed to be a long-acting IL-2Rβ biased agonist is "long-acting". For the purposes herein, the long acting nature of an IL-2Rβ biased agonist is typically determined using flow cytometry to measure STAT5 phosphorylation in lymphocytes at various time points after administration of the agonist to be evaluated in mice. As a reference, the signal is lost by around 24 hours with IL-2, but is sustained for a period greater than that for a long-acting IL-2Rβ-biased agonist. As an illustration, the signal is sustained over several days for the RSLAIL-2 compositions.

Considering now the IL-2Rβ bias of a long-acting agonist as described herein, Example 2 provides both in-vitro and in-vivo data related to receptor bias for exemplary compositions of RSLAIL-2. As described in Example 2, in a murine melanoma tumor model, the ratio of CD8/regulatory T cells for RSLAIL-2 when compared to IL-2 supports preferential activation of the IL-2 receptor beta over IL2 receptor alpha. Exemplary long-acting IL-2Rβ biased agonists such as RSLAIL-2 are, for example, effective to preferentially activate and expand effector CD8+ T- and NK-cells over Tregs.

Moreover, representative long-acting IL-2Rβ-biased agonists such as RSLAIL-2 provide increased tumor exposure, and preferably significantly enhanced tumor exposure relative to IL-2, for example, at least a 50-fold increased exposure, or at least a 100-fold increased exposure, or at least a 200-fold increased exposure, or at least a 300-fold increased exposure, or at least a 400-fold increased exposure, or at least a 500-fold increased exposure when normalized for equivalents of IL-2. As an illustration, the antitumor activity of RSLAIL-2 in a mouse melanoma tumor model is described in Example 3. As described therein, RSLAIL-2 was found to provide significantly enhanced tumor exposure, e.g., 500-fold, relative to IL-2 (normalized based upon IL-2 equivalents).

Methods

Based upon at least one or more of the features of a long-acting IL-2Rβ-biased agonist as described herein, provided herein are methods effective to induce an immune response in a cancer patient prior to administration of a long-acting IL-2Rβ-biased agonist by administering autologous or allogenic anti-tumor T cells or other cells as described herein that have been cultured and expanded ex vivo, followed by administration of a long-acting IL-2Rβ-biased agonist in which a region that interacts with the IL2Rα subunit responsible for activating immunosuppressive Tregs is masked, to thereby achieve superior therapeutic efficacy.

In accordance with the methods described herein, the long-acting, IL-2Rβ-biased agonist is provided in an IL-2Rβ-activating amount. One of ordinary skill in the art can determine how much of a given long-acting, IL-2Rβ-biased agonist is sufficient to provide clinically relevant agonistic activity at IL-2Rβ. For example, one of ordinary skill in the art can refer to the literature and/or administer a series of increasing amounts of the long-acting, IL-2Rβ-biased agonist and determine which amount or amounts provide clinically effective agonistic activity of IL-2Rβ. Alternatively, an activating amount of the long acting IL-2Rβ-biased agonist can be determined using the in vivo STAT5 phosphorylation assay described above (determined in vivo following administration) where an amount sufficient to induce STAT5 phosphorylation in greater than 10% of NK cells at peak is considered to be an activating amount.

In one or more instances, however, the IL-2Rβ-activating amount is an amount encompassed by one or more of the following ranges expressed in amount of protein: from about 0.01 to 100 mg/kg; from about 0.01 mg/kg to about 75 mg/kg; from about 0.02 mg/kg to about 60 mg/kg; from about 0.03 mg/kg to about 50 mg/kg; from about 0.05 mg/kg to about 40 mg/kg; from about 0.05 mg/kg to about 30 mg/kg; from about 0.05 mg/kg to about 25 mg/kg; from about 0.05 mg/kg to about 15 mg/kg; from about 0.05 mg/kg to about 10 mg/kg; from about 0.05 mg/kg to about 5 mg/kg; from about 0.05 mg/kg to about 1 mg/kg. In some embodiments, the long acting IL-2Rβ-biased agonist is administered at a dose that is less than or equal to 0.7 mg/kg. Particular illustrative dosing ranges include for example, from about 0.1 mg/kg to about 10 mg/kg, or from about 0.2 mg/kg to about 7 mg/kg or from about 0.2 mg/kg to less than about 0.7 mg/kg.

For confirmation, with respect to the long-acting, IL-2Rβ-biased agonist, the amount and extent of the activation can vary widely and still be effective when coupled with adoptive cell transfer therapy. That is to say, an amount of a long-acting, IL-2Rβ-biased agonist that exhibits only minimal agonist activity at IL-2Rβ for a sufficiently extended period of time can still be a long-acting, IL-2Rβ-biased agonist so long as when administered in combination with adoptive cell therapy, the methods described herein enable a clinically meaningful response. In some instances, due to (for example) synergistic interactions and responses, only minimal agonist activity of IL-2Rβ may be required when accompanied by adoptive cell transfer therapy.

In one or more embodiments, the adoptive cell transfer is carried out prior to administration of the long-acting, IL-2Rβ-biased agonist. For example, adoptive cell transfer-based cell infusion may occur immediately, up to 1 hour, up to 2 hours, up to 3 hours, up to 4 hours, up to 5 hours, up to 6 hours, up to 7 hours, up to 8 hours, up to 9 hours, up to 10 hours, up to 11 hours, up to 12 hours, up to 1 day, up to 2 days, up to 3 days, up to 4 days, up to 5 days, up to 6 days, up to 7 days, up to 8 days, up to 9, days, up to 10 days, up to 11 days, up to 12 days, up to 13 days, up to 14 days, up to 15 days, up to 16 days, up to 17 days, up to 18 days, up to 19 days, up to 20 days, up to 21 days, up to 22 days, up to 23 days, up to 24 days, up to 25 days, up to 26 days, up to 27 days, up to 28 days, up to 29 days, up to 1 month, up to 3 months, up to 6 months or any combination thereof prior to administration of the long-acting, IL-2Rβ-biased agonist.

The treatment methods described herein can continue for as long as the clinician overseeing the patient's care deems the treatment method to be effective. Non-limiting parameters that indicate the treatment method is effective include any one or more of the following: tumor shrinkage (in terms of weight and/or volume); a decrease in the number of individual tumor colonies; tumor elimination; and progression-free survival. Change in tumor size may be determined by any suitable method such as imaging. Various diagnostic imaging modalities can be employed, such as computed tomography (CT scan), dual energy CDT, positron emission tomography and MRI.

The actual dose of the long-acting, IL-2Rβ-biased agonist, as well as the dosing regimen associated with the methods described herein will vary depending upon the age, weight, and general condition of the subject as well as the type and progression of the cancer being treated, the judgment of the health care professional, and the particular adoptive cell transfer therapy employed and the long-acting, IL-2Rβ-biased agonist to be administered.

With regard to the frequency and schedule of adoptive cell transfer and administering of the long acting, IL-2Rβ-biased agonist, one of ordinary skill in the art will be able to determine an appropriate frequency. For example, in a treatment cycle, a clinician may conduct adoptive cell transfer in combination with administration of the long acting, IL-2Rβ-biased agonist, either concurrently with the adoptive cell transfer, or preferably, following adoptive cell transfer. For example, in some treatment modalities, the long acting, IL-210-biased agonist is administered within 7 days of adoptive cell transfer (e.g., on any one of days 1, 2, 3, 4, 5, 6, or 7). In some instances, the long acting, IL-2Rβ-biased agonist is administered within 4 days of adoptive cell transfer, e.g., on any one of days 1, 2, 3, or 4. Based upon the long acting nature of the IL-2Rβ-biased agonist, such compound is typically administered relatively infrequently (e.g., once every three weeks, once every two weeks, once every 8-10 days, once every week, etc.).

Exemplary lengths of time associated with the course of therapy include about one week; about two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about twenty-three months; about twenty-four months; about thirty months; about three years; about four years and about five years. Typically, a single round of adoptive cell transfer is provided to a patient, following by one or more doses of the long acting, IL-2Rβ-biased agonist, however, in some instances, one or more additional cycles of adoptive cell transfer may occur.

The treatment methods described herein are typically continued for as long as the clinician overseeing the patient's care deems the treatment method to be effective, i.e., that the patient is responding to treatment. Non-limiting parameters that indicate the treatment method is effective may include one or more of the following: tumor shrinkage (in terms of weight and/or volume and/or visual appearance); a decrease in the number of individual tumor colonies; tumor elimination; progression-free survival; appropriate response by a suitable tumor marker (if applicable), increased number of NK (natural killer) cells, increased number of T cells, increased number of memory T cells, increased number of central memory T cells, reduced numbers of regulatory T cells such as CD4+ Tregs, CD25+ Tregs, and FoxP3+ Tregs.

The methods provided herein are useful for (among other things) treating a patient suffering from cancer. For example, patients may be responsive to the adoptive cell transfer alone, as well as in combination with a long acting, IL-2Rβ-biased agonist, but are more responsive to the combination. By way of further example, patients may be non-responsive to either the adoptive cell transfer or the long acting, IL-2Rβ-biased agonist, but are responsive to the combination. By way of still further example, patients may be non-responsive to either of the adoptive cell transfer or the long acting, IL-2Rβ-biased agonist alone, but are responsive to the combination.

Administration of the long acting, IL-2Rβ-biased agonist is typically via injection. Other modes of administration are also contemplated, such as pulmonary, nasal, buccal, rectal, sublingual and transdermal. As used herein, the term "parenteral" includes subcutaneous, intravenous, intra-arterial, intratumoral, intralymphatic, intraperitoneal, intracardiac, intrathecal, and intramuscular injection, as well as infusion injections. As described previously, the adoptive cells and the long acting, IL-2Rβ-biased agonist can be administered separately. Alternatively, if provision of adoptive cell transfer and administration of the long acting, IL-2Rβ-biased agonist is desired to be simultaneous, either as an initial dose or throughout the course of treatment or at various stages of the dosing regimen—and the cells and the long acting, IL-2Rβ-biased agonist are compatible together and in a given formulation—then the simultaneous administration can be achieved via infusion of single dosage form/formulation (e.g., intravenous administration of an intravenous formulation that contains both immunological components).

Administration to a patient of the IL-2Rβ-biased agonist can be achieved through injection of a composition comprising, for example, the IL-2Rβ-biased agonist (e.g., RSLAIL-2) and a diluent. With respect to possible diluents, the diluent can be selected from the group consisting of bacteriostatic water for injection, dextrose 5% in water, phosphate-buffered saline, Ringer's solution, lactated Ringer's solution, saline, sterile water, deionized water, and combinations thereof.

The therapeutic combination described herein may also be provided in the form of a kit comprising the long acting IL-2Rβ-biased agonist accompanied by instructions for use in combination with adoptive cell transfer. As described above, the long acting IL-2Rβ-biased agonist may be comprised in a single dose composition, optionally accompanied by one or more pharmaceutically acceptable excipients. Suitable pharmaceutically acceptable excipients include those described, for example, in the Handbook of Pharmaceutical Excipients, $7^{th}$ ed., Rowe, R. C., Ed., Pharmaceutical Press, 2012. The kit components may be in either liquid or in solid form. In certain preferred embodiments, the long acting IL-2Rβ-biased agonist is in solid form. Preferred solid forms are those that are solid dry forms, e.g., containing less than 5 percent by weight water, or preferably less than 2 percent by weight water. The solid forms are generally suitable for reconstitution in an aqueous diluent, which may also be provided in the kit.

The presently described methods, kits and related compositions can be used to treat a patient suffering from any condition that can be remedied or prevented by the methods provided herein, such as cancer. The cancer may be a liquid cancer or a solid cancer. Exemplary conditions are cancers, such as, for example, melanoma, kidney, non-small cell lung breast cancer (e.g., triple negative breast cancer), bladder, head and neck cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, brain cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, Hodgkin lymphoma, non-Hodgkin lymphoma, testicular cancer, lung cancer, small cell lung cancer, brain cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma, multiple myeloma, neuroblastoma, retinoblastoma and leukemias.

In some particular embodiments, the cancer to be treated is a solid cancer.

In yet some further embodiments, the cancer to be treated is selected from, for example, breast cancer, ovarian cancer, colon cancer, prostate cancer, bone cancer, colorectal cancer, gastric cancer, lymphoma, malignant melanoma, liver cancer, small cell lung cancer, non-small cell lung cancer, pancreatic cancer, thyroid cancers, kidney cancer, cancer of the bile duct, brain cancer, cervical cancer, maxillary sinus cancer, bladder cancer, esophageal cancer, and adrenocortical cancer.

In yet one or more further embodiments, the cancer is selected from melanoma, kidney, non-small cell lung, breast, bladder, head and neck, and colon cancer.

In one or more particular embodiments, the breast cancer is triple negative breast cancer. Triple negative breast cancers are highly aggressive tumors that lack estrogen receptors, progesterone receptors, and ERBB2 (HER2) gene amplification.

The present methods, kits and compositions are useful for enhancing the therapeutic effectiveness of adoptive cell transfer, for example, by improving the subject's response, by administration of a long acting IL-2Rβ-biased agonist. An enhanced response may be evaluated at any suitable time point during treatment, after a single round of treatment, after 2-3 cycles of treatment, etc., and by any of a number of suitable methods, including shrinkage of a tumor (partial response), i.e., an evaluation of tumor size or volume, disappearance of a tumor, a reduction in disease progression (cancer has not progressed), and analysis of one or more tumor test markers if appropriate. In some instances, an indication of efficacy of treatment can be measured in terms of a time delay between 50% maximum tumor growth when comparing treatment with adoptive cell transfer and a long-acting IL-2Rβ-biased agonist such as RSLAIL-2 to treatment with either adoptive cell transfer alone, the long-acting IL-2Rβ-biased agonist alone, or treatment with a combination of adoptive cell transfer and a corresponding non-long acting version of IL-2 (e.g., dosed to achieve a comparable number of IL-2 equivalents). The comparison may be conducted in a human patient, or in a suitable animal model such as a suitable murine model of cancer.

The methods, kits, compositions and combination provided herein are also useful for reducing tumor growth or size (or volume) in a subject undergoing treatment. Treatment that employs adoptive cell transfer in combination with administration of a therapeutically effective amount of a long-acting IL-2Rβ-biased agonist such as provided herein to a subject having established tumors is effective, in one or more embodiments, to reduce tumor growth or size in the subject. For example, in some embodiments, one or more cycles of treatment is effective to reduce tumor size by about 25%, or by about 30%, or by about 40%, or by about 50%, or even by about 60%, or by about 70% or more when compared to the size of the tumor prior to treatment.

In yet some further embodiments, the methods, kits, compositions and combination provided herein are effective to inhibit accumulation of regulatory T cells (Tregs) in a subject undergoing treatment for cancer. In some embodiments, the method is effective, for example, when evaluated in a cancer mouse model of the corresponding cancer, to inhibit accumulation of regulatory T cells selected from the group consisting of CD4+ Tregs, CD25+ Tregs, and FoxP3+ Tregs in the tumor (i.e., any one or more of the foregoing cell types) by an amount that is enhanced over that observed upon administration of either ACT alone, the long-acting IL-2Rβ-biased agonist alone, or treatment with a combination of ACT and a corresponding non-long acting version of IL-2 (e.g., dosed to achieve a comparable number of IL-2 equivalents).

In yet some further embodiments, the methods, kits, composition and combination provided herein are effective to stimulate T cell and/or NK cell activity and/or proliferation in a subject. In some embodiments, the method is effective, for example, when evaluated in a cancer mouse model of the corresponding cancer, for increasing the number of CD8+ T cells in the subject. In yet some other embodiments, the method is effective, for example, when evaluated in a cancer mouse model of the corresponding cancer, to increase the number of NK cells in the subject.

Turning to the Examples, Examples 4 and 5 describe the evaluation of anti-tumor activity of RSLAIL-2 in combination with adoptive cell transfer in an aggressive murine melanoma model. As described in detail in such examples, treatment with the illustrative long-acting IL-2Rβ-biased agonist, RSLAIL-2, in combination with adoptive cell transfer was found (among other things) to robustly mobilize T cells into the tumor, where they durably persist. Moreover, the effect was significantly pronounced when compared to a group similarly treated with an adoptive cell transfer/non-long acting IL-2 combination. Not only was the tumor growth delay significantly enhanced for the ACT/RSLAIL-2 combination therapy group (when compared to control and an ACT/IL-2 combination), but increased T cell expansion in the spleen, where tumor homing was also observed for the RSLAIL-2 treatment group. As these results suggest, the combination of adoptive cell therapy and the long-acting IL-2Rβ-biased agonist, RSLAIL-2, are biased to effector cells which persist, not only after a single dose of the long-acting IL-2Rβ-biased agonist, but also after multiple doses. Moreover, this effector cell bias is observed specifically in the tumor when compared to normal tissue, and is significant when compared to adoptive cell transfer combined with interleukin-2 treatment as supported by independent analytical methods including imaging, flow cytometry, and IHC. Additionally, the persistence of effector cells is shown by the length of the time points post-dose and also by a robust response that is maintained after multi-doses of the long-acting IL-2Rβ-biased agonist (in comparison to administration of IL-2, where the response falls off with subsequent doses). The combination immunotherapy described herein, in contrast to many ACT-based therapies, is effective to increase the extent and persistence (i.e., retention) of exogenously delivered effector cells at a tumor site, to thereby provide increased antitumor efficacy.

Thus, in yet a further aspect, provided herein is a method of increasing retention of exogeneously-introduced effector T cells in a subject, comprising (i) introducing to a subject having a cancerous tumor, lymphocytes that have been obtained from the cancerous tumor of the subject, cultured, and expanded ex vivo, and (ii) administering to the subject an IL-2Rβ-activating amount of a long-acting IL-2Rβ-biased agonist, to thereby result in a greater number of the introduced lymphocytes retained at the tumor site when compared to the number of introduced lymphocytes retained at the tumor site upon treatment of the subject with the lymphocytes from step (i) alone, i.e., absent administration of the long-acting IL-2Rβ-biased agonist or when compared to the number of introduced lymphocytes retained at the tumor site upon treatment of the subject with the lymphocytes from step (i) in combination with administration of a non-long acting version of interleukin-2 (e.g., dosed to achieve a comparable number of IL-2 equivalents).

The number of introduced lymphocytes retained at the tumor site can be measured at any suitable time point following administration of the long-acting IL-2Rβ-biased agonist, for instance, at day 1, day 2, day 3, day 4, day 5, day 6, day 7, day 8, day 9, day 10, day 11, day 12, day 13, day 14, day 15, day 16, day 17, day 18, day 19, day 20 and so forth, following the first administration of the long-acting IL-2Rβ-biased agonist. In some preferred embodiments, the number of introduced lymphocytes is measured at any one of days 10, 11, 12, 13, 14, 15, or 16, following the first administration of the long-acting IL-2Rβ-biased agonist, using any suitable method for assessing numbers of cells. Suitable methods include but are not limited to image analysis, flow cytometry, and IHC.

All articles, books, patents, patent publications and other publications referenced herein are incorporated by reference in their entireties. In the event of an inconsistency between the teachings of this specification and the art incorporated by reference, the meaning of the teachings and definitions in this specification shall prevail (particularly with respect to terms used in the claims appended herein). For example, where the present application and a publication incorporated by reference defines the same term differently, the definition of the term shall be preserved within the teachings of the document from which the definition is located.

EXAMPLES

It is to be understood that the foregoing description as well as the examples that follow are intended to illustrate and not limit the scope of the disclosure. Other aspects, advantages and modifications within the scope of the invention(s) will be apparent to those skilled in the art to which the disclosure pertains.

Materials and Methods

Recombinant human IL-2 having an amino acid sequence identical to that of aldesleukin was cloned and expressed and used to prepare the exemplary long-acting IL-2Rβ-biased agonist referred to herein as RSLAIL-2.

RSLAIL-2 refers to a composition obtainable upon following the procedures of Example 1 in PCT Int. Pat. Appl. Pub. No. WO 2015/125159, and generically refers to a composition comprising multi-PEGylated forms of IL-2, wherein attachment of the PEG reagent used to form the conjugates is releasable following administration to a subject. See also Example 1 below.

Example 1

PEGylation of rIL-2 with
mPEG2-C2-Fmoc-20kD-NHS

Purified rIL-2 (106.4 mL) at 1.44 mg/ml was charged into a first vessel followed by the addition of 53.6 mL of formulation buffer (10 mM sodium acetate, pH 4.5, 5% trehalose). The pH was measured at 4.62 the temperature was measured at 21.2° C. The PEG reagent, C2-PEG2-FMOC-NHS-20K (available as described in WO 2006/138572) (13.1 g), was charged into a second vessel followed by the addition of 73.3 mL of 2 mM HCl. The resulting solution was swirled by hand for 25 minutes. Sodium borate (0.5 M, pH 9.8) was added to the first vessel to raise the pH to about 9.1 and then the contents of the second vessel containing the PEG reagent was added to the first vessel over a period of from one to two minutes. A rinse step was then performed by charging 8.1 mL of 2 mM HCl into the second vessel and adding the contents to the first vessel. For the conjugation reaction, the final rIL-2 concentration was 0.6 mg/mL, the sodium borate concentration was 120 mM, the pH was 9.1+/−0.2, the temperature was 20-22° C., and the molar ratio of PEG reagent to rIL-2, after adjustment for activity of the reagent (substitution level) was 35:1. The conjugation reaction was allowed to proceed for thirty minutes and quenched by acidification by addition of 75 mL of 2N acetic acid (to bring the pH down to approximately to 4). The product was purified by ion exchange chromatography as previously described to provide a composition of primarily 4-mers, 5-mers and 6-mers (referring to the number of PEG reagents releasably covalently attached to r-IL-2 (wherein 8-mers and higher degrees of PEGylation were removed during a washing step associated with chromatography). This composition is referred to herein as "RSLAIL-2."

Example 2

Receptor-Bias of RSLAIL-2 and Related
Immunotherapeutic Properties

Binding Affinity to IL-2 Receptors and Receptor Bias Related to Immunostimulatory Profile: The affinity of RSLAIL-2 to IL-2Rα and IL-2Rβ was measured directly by surface plasmon resonance (Biacore T-100) and compared to that of clinically available IL-2 (aldesleukin). Antihuman antibody (Invitrogen) was coupled to the surface of a CM-5 sensor chip using EDC/NHS chemistry. Then either human IL-2Rα-Fc or IL-2Rβ-Fc fusion protein was used as the captured ligand over this surface. Serial dilutions of RSLAIL-2 and its active IL-2 conjugates metabolites (1-PEG- and 2-PEG-IL-2) were made in acetate buffer pH 4.5, starting at 5 mM. These dilutions were allowed to bind to the ligands for 5 minutes, and the response units (RU) bound was plotted against concentration to determine EC50 values. The affinities of each isoform to each IL-2 receptor subtype were calculated as fold change relative to those of IL-2.

The in vitro binding and activation profiles of RSLAIL-2 suggested that PEGylation interferes with the interaction between IL2 and IL2Rα relative to aldesleukin; an investigation was carried out to determine whether these effects bias the profile of immune cell subtypes in vivo. The number of CD8 T and Treg cells in a tumor following administration of either RSLAIL-2 or IL2 is an important measure of whether pleiotropic effects of IL2 have been shifted due to conjugation of IL2 to poly(ethylene glycol) (as in RSLAIL-2) at the IL2/IL2Rα interface. To address the question, mice bearing subcutaneous B16F10 mouse melanoma tumors were treated with a single dose of RSLAIL-2 or 5 doses of aldesleukin, and immune cells in the tumor microenvironment were quantified by flow cytometry. Results are shown in FIGS. 1A-1G.

In tumors of aldesleukin-treated mice, total and memory CD8 cells were increased as a percentage of tumor-infiltrating lymphocytes; however, these effects were transient, reaching significance relative to vehicle on day 5. In contrast, significant (P<0.05) and sustained total and memory CD8 T-cell stimulation was achieved following a single RSLAIL-2 administration, with superior percentages of memory CD8 (day 7) and total CD8 (days 7 and 10) relative to aldesleukin. Both RSLAIL-2 and aldesleukin treatment resulted in increased activated natural killer (NK) cells 5 and 7 days after treatment initiation, though this effect was diminished by day 10. CD4 cell percentages of tumor-infiltrating lymphocytes were diminished following RSLAIL-2 treatment relative to vehicle on day 5. On day 10, RSLAIL-2 resulted in fewer CD4 cell percentages compared with vehicle and aldesleukin. The CD4 cell population was further analyzed for the FoxP3$^+$ subset, which defines the Treg population. RSLAIL-2 administration reduced percentage of Tregs at every time point, consistent with reduced access to the IL2Rα subunit arising from the PEG chains. In contrast, Treg reduction with aldesleukin was modest achieving significance on day 5. The increase of CD8 T cells and reduction of Tregs led to a marked elevation of the CD8/Treg ratio in the tumor by day 7. The ratio of CD8/Treg for RSLAIL-2, aldesleukin, and vehicle was 449, 18, and 4, respectively, supporting preferential activation of the IL2 receptor beta over IL2 receptor alpha for RSLAIL-2.

Immunohistochemical staining was performed and confirmed that CD8 T cells were not only increased in number but were interspersed with tumor cells. These results indicate RSLAIL-2 is effective to induce a more robust in vivo memory effector CD8 T-cell response than seen with unmodified IL-2 (aldesleukin), without a commensurate stimulation of Tregs in tumor, consistent with an in vitro IL2Rβ-biased binding profile. That is to say, RSLAIL-2 is effective to preferentially activate and expand effector CD8+ T- and NK-cells over Tregs.

Example 3

Tumor Exposure of RSLAIL-2

The objective of this study was to evaluate the antitumor activity of RSLAIL-2 in C57BL/6 mice implanted with B16F10 melanoma cells when compared to aldesleukin.

C57BL/6 mice were implanted subcutaneously into the right flank with B16F10 melanoma cells ($1\times10^6$ per animal). Seven days after implantation, when tumors measured 200 mm³, animals were administered RSLAIL-2 (2 mg/kg×1) or aldesleukin (3 mg/kg daily×5). Tumors were harvested (n=4 per observation time), homogenized in ice-cold PBS containing protease inhibitor (Roche) and 0.25% acetic acid, and centrifuged to obtain supernatant. To quantify RSLAIL-2 levels in tumor tissue, PEG was released from IL2 by incubating the supernatant in a pH 9 buffer at 37° C. overnight. IL2 was measured by sandwich ELISA specific for human IL2. To calculate AUC, data were fit with Pheonix WinNonLin using a noncompartmental model. AUC after aldesleukin was estimated on the basis of day 1 AUC multiplied by 5.

As shown in FIG. 2, tumor aldesleukin levels rapidly reached $C_{max}$ and then rapidly declined, leading to <4 ng/g concentrations 24 hours after each dose and a daily AUC of 0.09±0.02 m/hour/g. In contrast, RSLAIL-2 was detectable in tumors for up to 8 days after a single dose achieving an AUC of 30±6.9 m/hour/g. On the basis of AUC, a single dose of RSLAIL-2 led to a 67-fold higher exposure compared with 5 daily doses of aldesleukin, even though 7.5 fewer IL2 equivalents were dosed using RSLAIL-2 (3 mg/kg daily×5=15 mg/kg vs. 2 mg/kg). Thus, normalizing exposure on the basis of IL2 equivalents, RSLAIL-2 achieved a 500-fold increased exposure relative to aldesleukin. The active conjugated IL-2 form of RSLAIL-2 (2-PEG-IL2 and 1-PEG-IL2 together) was also quantified and remained detectable in tumor for up to 5 days yielding an AUC of 23±4.4 m/g. Hence, exposure to active conjugated IL2 was 50-times higher compared with aldesleukin, translating to 380 times increased exposure relative to an equivalent dose of aldesleukin. The tumor exposure of RSLAIL-2 thus allowed dosing once every 9 days in mice compared with twice daily for two 5-day cycles for aldesleukin.

Example 4

Evaluation of Antitumor Activity of RSLAIL-2 in Combination with ACT in an Aggressive Murine Melanoma Model A pmel-1 ACT/BL6 melanoma tumor model was used to test the anti-tumor activity of RSLAIL-2 and evaluate its effects on tumor-specific TCR transgenic T cells. On Day 0 (D0) C57/BL6 mice were implanted with B16-F10 mouse melanoma cells after lympho-depletion with 500 cGy dose of ionizing radiation on D6 (Day 6). On D7, mice were treated with the combination of ACT (T lymphocytes activated in vitro with 1 μg/ml antigen gp100) plus RSLAIL-2 (0.8 mg/kg, q9d×3, i.v.) or with C57/BL6 T cells plus PBS (vehicle control). The tumors of the vehicle control mice (n=12) rapidly grew to the 1500 mm³ endpoint in 12 days post-treatment, versus 35 days for the RSLAIL-2/ACT combination group (n=12) where only 1/12 reached endpoint. Bioluminescence imaging was used to visualize the in vivo distribution and tumor-homing of antigen-specific T cells. Interestingly, after RSLAIL-2/ACT administration, the reporter T cells were retained in the spleen until D7 and could be seen migrating to the tumor at D9 reaching peak bioluminescence at D12, a delayed time point compared to the 5 days usually observed in mice treated with conventional IL-2. The signal persisted until D20 versus D7 in the vehicle-control animals. These data suggest RSLAIL-2 in combination with ACT is well tolerated and provides a robust anti-tumor response in the aggressive B16F10 murine melanoma model. Treatment with RSLAIL-2 and ACT therapy robustly mobilizes T cells into the tumor where they durably persist. The robust and long-lasting effect of RSLAIL-2 supports its use in combination with cell-based therapeutics.

Similar studies are conducted with B16-A2/K murine melanoma or EL-4-A2/K murine lymphoma tumors engineered to express a chimeric murine/human MHC molecule.

Example 5

Figure 3:
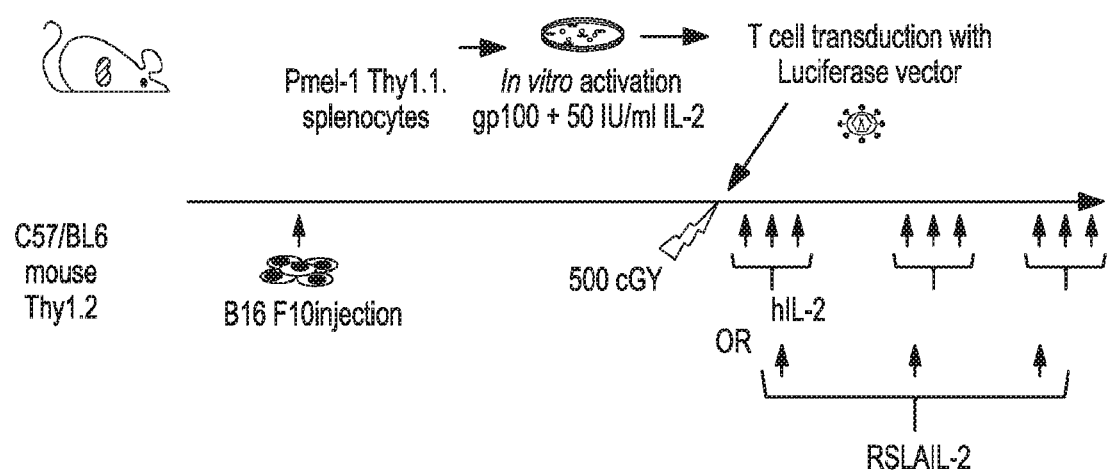
FIG. 3 is a schematic describing the dosing strategy employed in Example 5 in which the anti-tumor activity of RSLAIL-2 or IL-2 in combination with pmel-1 adoptive cell transfer was investigated in an aggressive murine melanoma model.

Evaluation of Antitumor Activity of RSLAIL-2 or IL-2 in Combination with ACT in a Murine Melanoma Model C57/BL6 mice were implanted subcutaneously with B16F10 ($0.5\times10^6$ per animal) syngeneic murine melanoma cell line on D−7 (day minus 7) and lymphodepleted with a 500 cGy dose of ionizing radiation on D−1 (day minus 1). On D0 (day 0), mice were treated with the combination of ACT (pmel-1 gp100 TCR transgenic T lymphocytes activated in vitro with 1 μg/ml gp100) and RSLAIL-2 (0.8 mg/kg, q9d×3, i.v.) or with IL-2 (aldesleukin, 0.4 mg/kg, qd×3 every 9 days for 3 cycles, i.p.), or vehicle. The second and third treatment cycle did not include ACT. The vehicle control was the same as in Example 4. FIG. 3 provides a schematic describing the dosing strategy employed.

Figure 4:
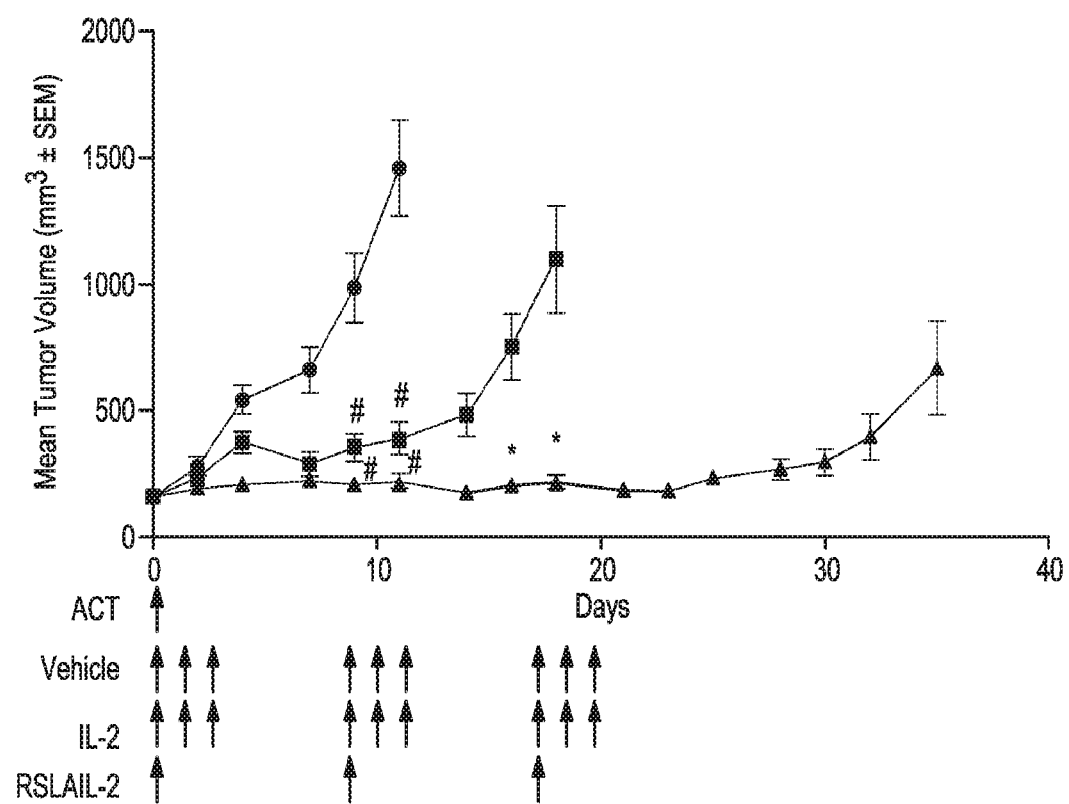
FIG. 4 provides a plot of mean tumor volume ($mm^3$) as determined by SEM versus time for the study described in Example 5. A schematic of the dosing regimen is provided by the arrows under the horizontal axis. Legend: solid circles: ACT+Vehicle; solid squares: ACT+IL-2; solid triangles: ACT+RSLAIL-2. As can be seen from the results shown in FIG. 4, RSLAIL-2 when administered in combination with adoptive cell transfer provided significant tumor growth delay when compared to IL-2 in combination with adoptive cell transfer with less frequent dosing ($p<0.0001$ when compared to ACT in combination with IL-2); (#$p<0.0001$ compared to vehicle (pair-wise comparison using Bonferroni test).

As can be seen from the results shown in FIG. 4 (a plot of mean tumor volume (mm³) as determined by SEM versus time), RSLAIL-2 when administered in combination with ACT provided significant tumor growth delay when compared to IL-2 in combination with ACT with less frequent dosing (p<0.0001 when compared to ACT in combination with IL-2); (#p<0.0001 compared to ACT in combination with vehicle (pair-wise comparison using Bonferroni test). When considering the plot, solid circles represent ACT+ Vehicle (top plot); solid squares represent ACT+IL-2 (middle plot); and solid triangles represent ACT+RSLAIL-2 (bottom plot with essentially no notable tumor growth until after about day 25.

Figure 5:
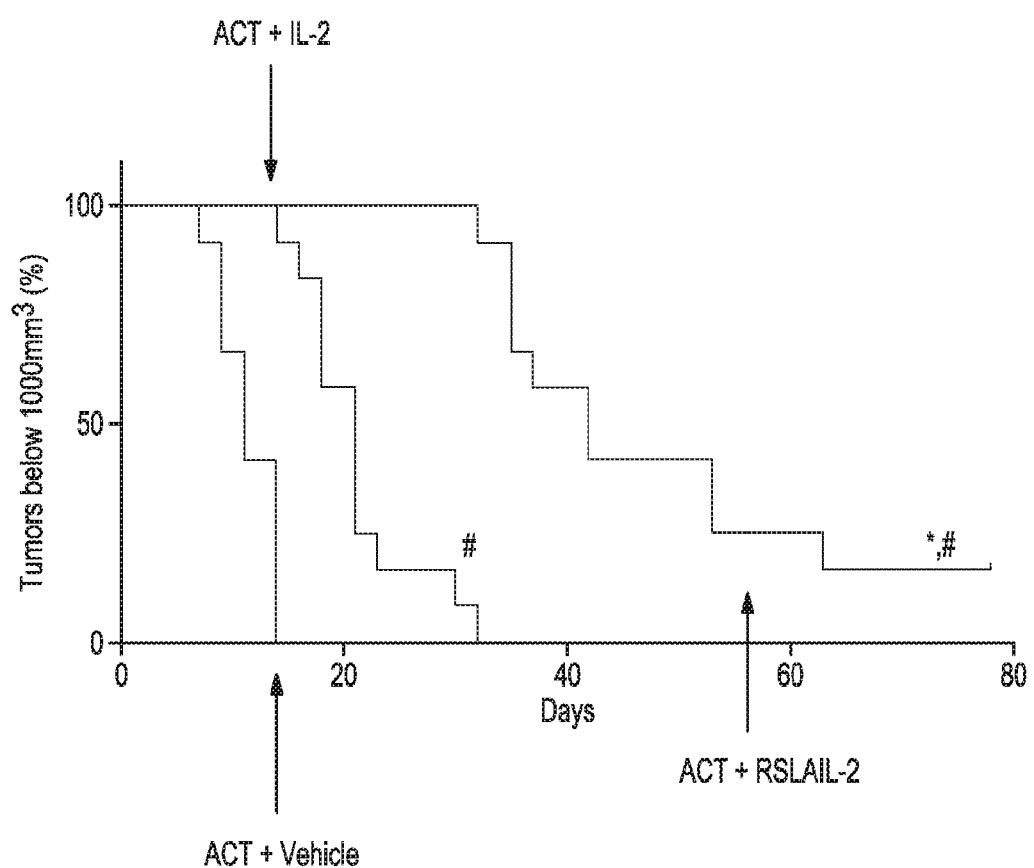
FIG. 5 illustrates tumor growth delay as assessed for each tumor growth curve by interpolating the time to achieve s tumor volume of 1000 $mm^3$ (*$p<0.0001$ compared to ACT+ IL-2; #$p<0.0001$ compared to vehicle (Log-Rank Mantel-Cox test) with N=12/group for the study described in Example 5.

Tumor growth delay was further assessed as illustrated in FIG. 5, where tumor growth delay was assessed for each tumor growth curve by interpolating the time to achieve tumor volume of 1000 mm³ (*p<0.0001 compared to ACT+ IL-2; #p<0.0001 compared to vehicle (Log-Rank Mantel-Cox test); N=12/group. The plot on the furthermost left represents the treatment group administered ACT in combination with vehicle; the middle plot represents the treatment group receiving ACT in combination with IL-2; the plot farthest to the right represents the treatment group that was administered ACT in combination with RSLAIL-2, which demonstrates the most notable tumor growth delay when compared to the other two treatment groups. As can be seen, the most significant tumor growth delay was observed for the combination of RSLAIL-2 and ACT.

In vivo Bioluminescence Imaging: In vivo bioluminescence imaging (BLI) of adoptively transferred lymphocytes was conducted. The Pmel-1 transgenic T cells were transduced with a retrovirus-firefly luciferase and used for ACT to allow visualization. In contrast to the ACT/vehicle or ACT/IL-2 groups, for the ACT/RLSAIL-2 combination, representative figures on days 5 and 14, five replicate mice per group, demonstrated T cell expansion in the spleen and mobilization to and persistence in the tumor.

Figure 6A:
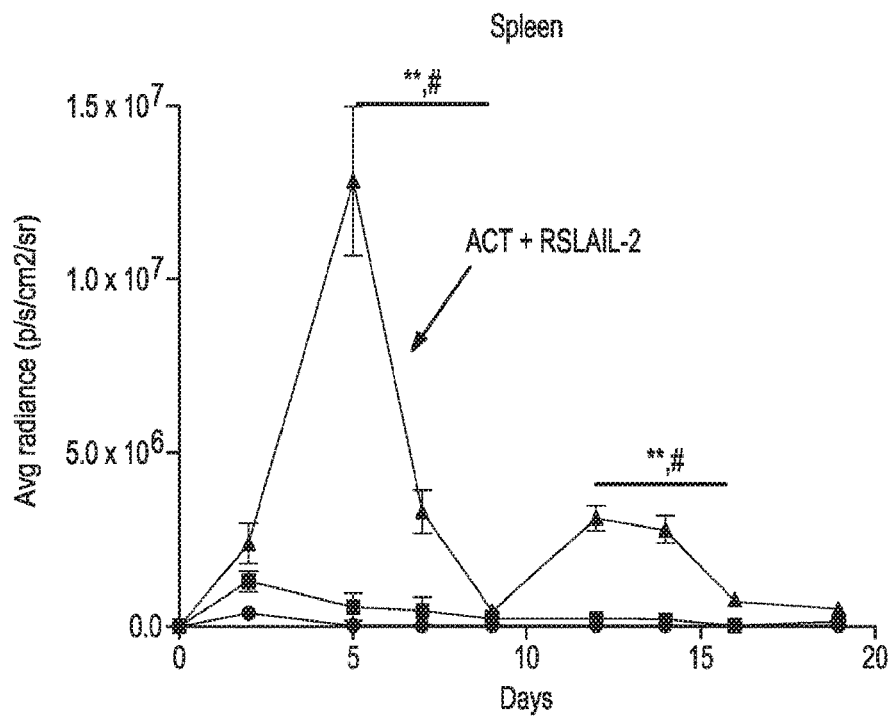
FIGS. 6A and 6B provide quantification of serial images in the region of interest (ROI) of spleen (FIG. 6A) and tumor (FIG. 6B) (counts per pixel) through day 19 following adoptive cell transfer of pmel-1 T cells expressing luciferase as described in Example 5 for in vivo bioluminescence imaging experiments. The figure legend is the same for both
Figure 6B:
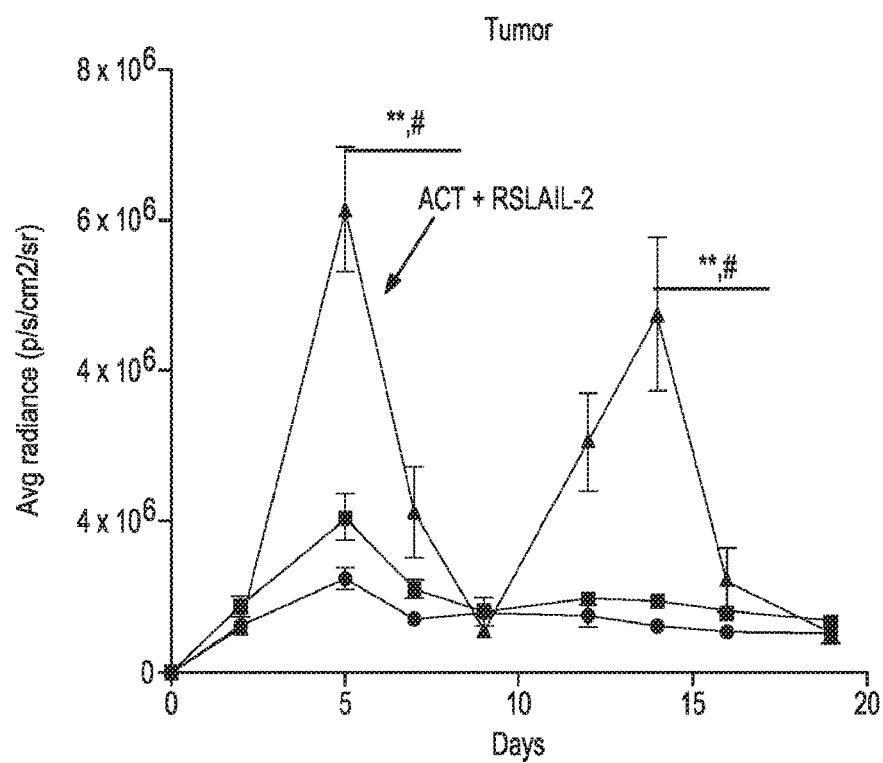

FIGS. 6A and 6B provide quantification of serial images in the region of interest (ROI) of spleen (FIG. 6A) and tumor (FIG. 6B) (counts per pixel) through day 19 following ACT of pmel-1 T cells expressing luciferase. FIG. 6A: Top plot, solid triangles: ACT+RSLAIL-2 as indicated; middle plot, solid squares: ACT+IL-2; bottom plot, solid circles: ACT+vehicle; FIG. 6B: Top plot, solid triangles: ACT+RSLAIL-2 as indicated; middle plot, solid squares: ACT+IL-2; bottom plot, solid circles: ACT+vehicle).

A single ACT+RSLAIL-2 treatment showed a statistically significant increase in T cell expansion in the spleen (FIG. 6A) from day 5 to day 9 when compared to 3 daily doses of IL-2+ACT or vehicle. The luciferase signal over time showed a stronger peak of tumor-infiltrating effector T cells in the ACT+RSLAIL-2 treatment group when compared to the ACT+IL-2 or ACT+vehicle treatment groups from day 5 to day 7. The second dose of RSLAIL-2 administered at day 9 triggered a second expansion of effector T cells in the spleen (FIG. 6A) and in the tumor (FIG. 6B) from day 12 to day 17. In contrast, there was no expansion in spleen or tumor after the second IL-2 treatment. (**$p<0.0001$ compared to IL-2+ACT, #$p<0.0001$ compared to ACT+vehicle, pair-wise comparison using Tukey test, n=5, mean±SE).

Figure 7A:
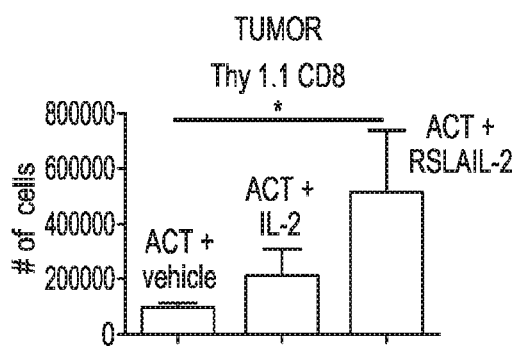
FIGS. 7A-7C are plots of numbers of immune cells in the tumor for the various treatment groups as described in Example 5, wherein the effect of adoptive cell transfer combination therapy (i.e., with either IL-2 or RSLAIL-2, or with control vehicle) on regulatory T cells and CD8+ T cells in the tumor was assessed by flow cytometry. In particular.
Figure 7B:
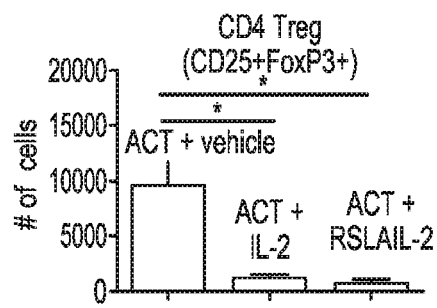
Figure 7C:
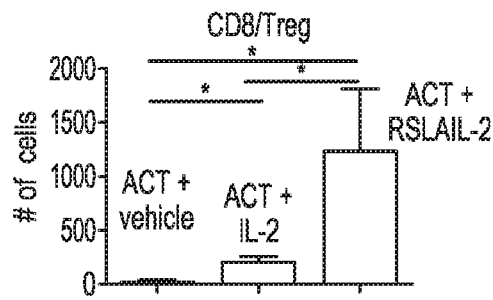

Tumor and Spleen Immunological Analysis: Tumors and spleens were collected on day 5 after treatment (single dose RSLAIL-2 and qd×3 of IL-2). The effect of RSLAIL-2 on regulatory T cells and CD8+ T cells was assessed by flow cytometry. FIGS. 7A-7B are plots illustrating the number of certain types of immune cells in the tumor; FIG. 7C provides the CD8/Treg ratio (tumor) for each of the treatment groups. Similarly, FIGS. 8A-8B are plots indicating the numbers of immune cells in the spleen, while FIG. 8C provides the CD8/Treg ratio (spleen) for each of the treatment groups.

More specifically, FIG. 7A illustrates the number of Thy 1.1 CD8 cells in the tumor for each of the treatment groups (progressing from left to right per bar, ACT+vehicle; ACT+IL-2 and ACT+RSLAIL-2). FIG. 7B illustrates the number of CD4 T regs in the tumor for each of the treatment groups (progressing from left to right per bar, ACT+vehicle; ACT+IL-2 and ACT+RSLAIL-2). FIG. 7C provides a ratio of the number of CD8 cells to Tregs in the tumor for each of the treatment groups as described above.

Figure 8A:
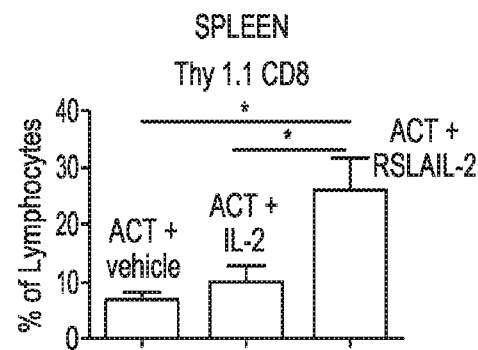
FIGS. 8A-8C illustrate the effect of ACT combination therapy (i.e., with either IL-2 or RSLAIL-2, or with control vehicle) on regulatory T cells and CD8+ T cells in the spleen as assessed by flow cytometry as detailed in Example 5. Specifically.
Figure 8B:
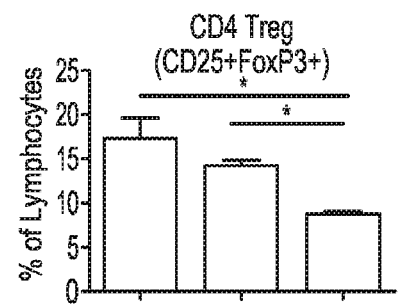
Figure 8C:
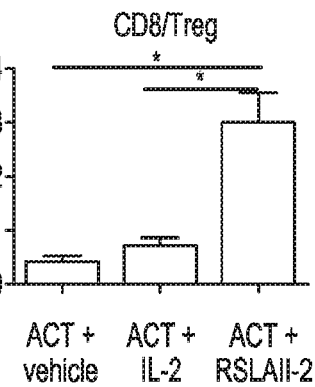

Turning now to the spleen, FIG. 8A illustrates the number of Thy 1.1 CD8 cells in the spleen for each of the treatment groups (progressing from left to right per bar, ACT+vehicle; ACT+IL-2 and ACT+RSLAIL-2). FIG. 8B illustrates the number of CD4 T regs in the spleen for each of the treatment groups (progressing from left to right per bar, ACT+vehicle; ACT+IL-2 and ACT+RSLAIL-2). FIG. 8C provides a ratio of the number of CD8 cells to Tregs in the spleen for each of the treatment groups as described above.

In the tumor, the absolute number of immune cells was normalized to tumor weight (grams) and graphed. Based on the results, it was discovered that ACT+RSLAIL-2 treatment increased pmel-1 CD8 T cells and amplified the CD8/Treg ratio when compared to the ACT+IL-2 or ACT+vehicle treatment groups. The CD8/Treg ratio was greater in the tumor than in the spleen for the RSLAIL-2 treatment group. Unpaired t test (**, $p<0.05$ with bars indicating comparisons, n=3).

Figure 9:
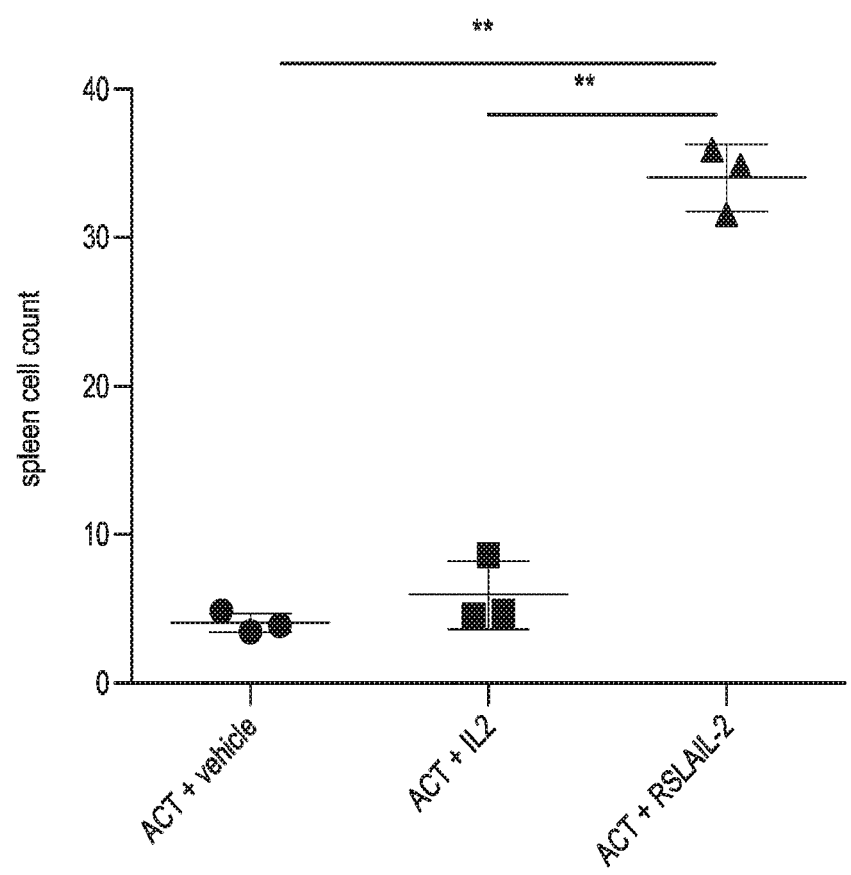
FIG. 9 is a graphical depiction showing splenic cell recovery at day 5 following treatment for each of the treatment groups as described in Example 5.

It was also observed that splenic cell recovery after irradiation was rapid for the ACT+RSLAIL-2 treatment group when compared to the ACT+IL-2 treatment group upon determination of splenocyte counts at day 5 after treatment. That is to say, RSLAIL-2 induced a rapid splenic cell repopulation after irradiation. Unpaired t test (**, $p<0.0001$ with bars indicating comparisons). See FIG. 9.

Figure 10:
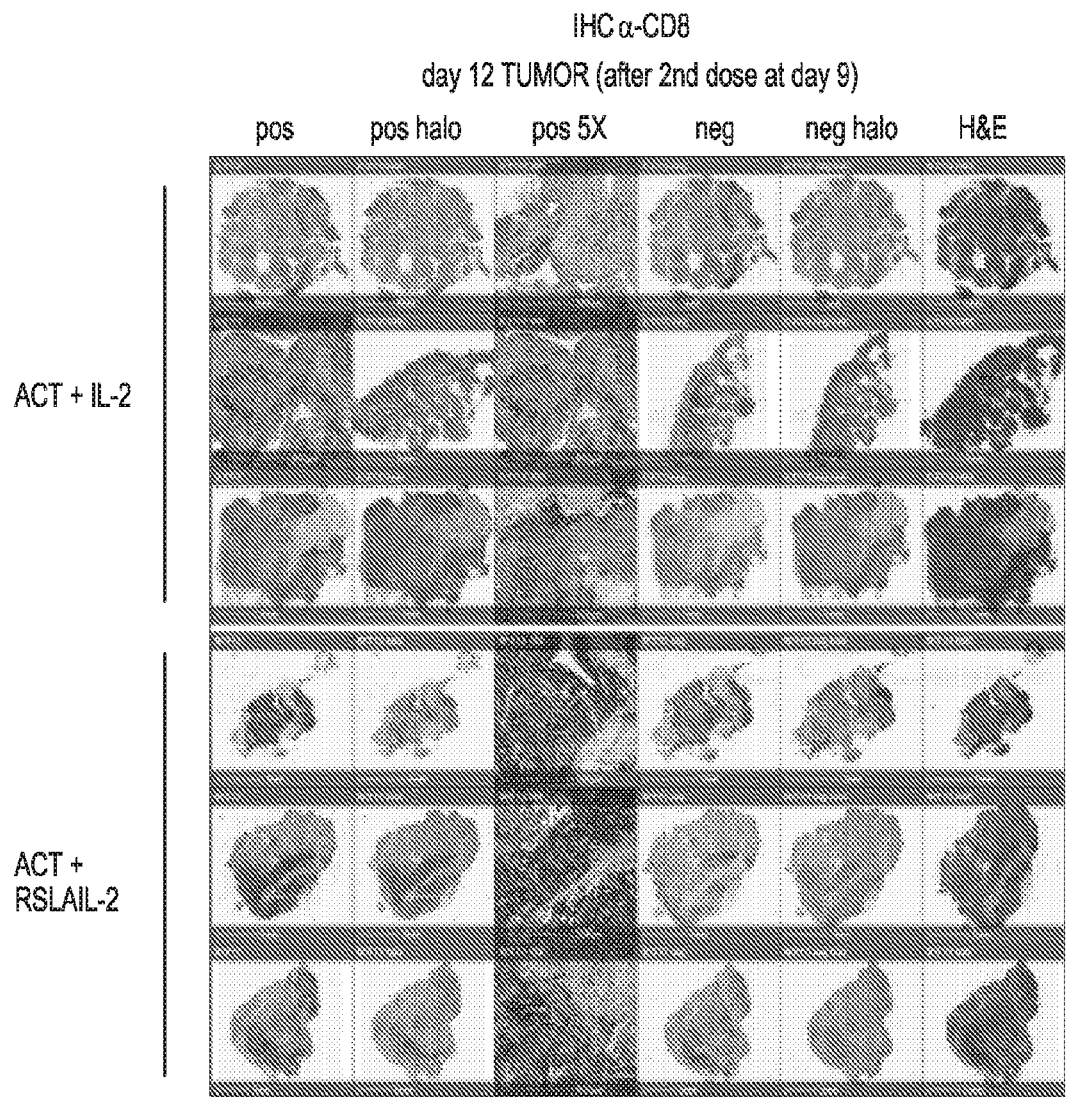
FIG. 10 is an IHC (immunohistochemistry) of the tumor at day 12 after administration of either IL-2 or RSLAIL-2 following adoptive cell transfer as described in Example 5. Immunohistochemical staining was performed on formalin-fixed/paraffin embedded tissues with murine anti-CD8 antibody; analysis was conducted using HALO image analysis software (Indica Labs, New Mexico). The figure shows CD8 infiltration in tumors of 3 different mice per group. The first column ("pos") shows the CD8 staining, the second column ("pos halo") is the slide analyzed by the HALO software, where in the color version, the blue dots are negative cells and the yellow to red dots are the CD8 positive cells (where yellow is low CD8 expression and red is high), the third column is a 5× magnification of a region positive for CD8 T cells. Columns 4 and 5 are the negative staining of the antibody anti-CD8, normal staining and HALO analysis, respectively. Column 6 is the H&E staining. The dark areas in column 1 correspond to the yellow and red dots in column 2 in the color version for the ACT+RSLAIL-2 combination therapy. This figure demonstrates a notable difference in CD8 expression between the two groups, with CD8 expression levels notably higher for the ACT+RSLAIL-2 combination therapy. The IHC illustrates persistence of intra-tumoral CD8 T cells in the case of treatment with a long-acting biased IL-2Rβ-interleukin-2 (RSLAIL-2) when compared to treatment with a non-polymer modified IL-2, aldesleukin.

Immunohistochemical staining was performed on formalin-fixed/paraffin embedded tissues with murine anti-CD8 antibody; analysis was conducted using HALO image analysis software (Indica Labs, New Mexico). FIG. 10 is an IHC (immunohistochemistry) of the tumor at day 12. The figure shows CD8 infiltration in tumors of three different mice per group. The first column ("pos") shows the CD8 staining, the second column ("pos halo") is the slide analyzed by the HALO software, where in the color version, the blue dots are negative cells and the yellow to red dots are the CD8 positive cells (where yellow is low CD8 expression and red is high), the third column is a 5× magnification of a region positive for CD8 T cells. Columns 4 and 5 are the negative staining of the antibody anti-CD8, normal staining and HALO analysis, respectively. Column 6 is the H&E staining. The dark areas in column 1 correspond to the yellow and red dots in column 2 in the color version for the ACT+RSLAIL-2 combination therapy. This figure demonstrates a notable difference in CD8 expression between the two groups, with CD8 expression levels notably higher for the ACT+RSLAIL-2 combination therapy. The IHC illustrates persistence of intra-tumoral CD8 T cells in the case of treatment with a long-acting biased IL-2Rβ-interleukin-2 (RSLAIL-2) when compared to treatment with a non-polymer modified IL-2, aldesleukin.

Figure 11:
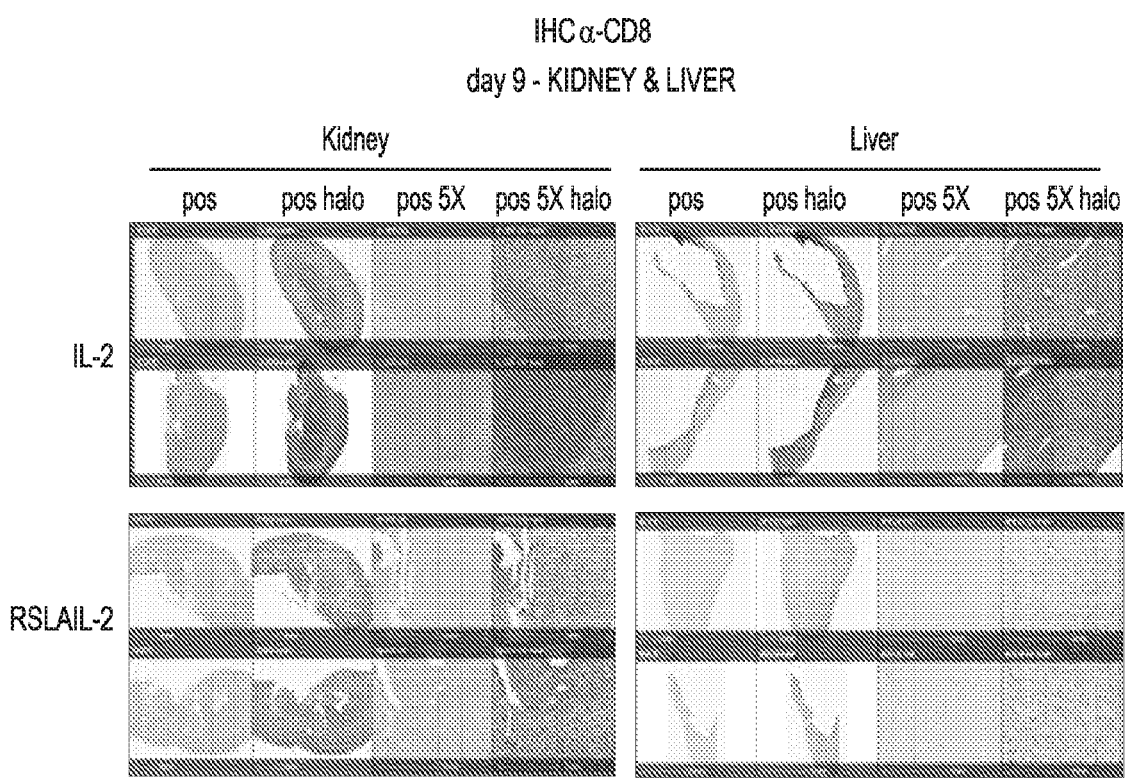
FIG. 11 is an IHC of normal, non-tumor tissue (kidney and liver) showing lack of tissue-damaging CD8 T cells at day 9 after one dose of either IL-2 (aldesleukin) or RSLAIL-2 following adoptive cell transfer as described in Example 5. Immunohistochemical staining was performed on formalin-fixed/paraffin embedded tissues with murine anti-CD8 antibody; analysis was conducted using HALO image analysis software (Indica Labs, New Mexico).

FIG. 11 is an IHC of normal, non-tumor tissue (kidney and liver) showing a lack of tissue-damaging CD8 T cells at day 9 after one dose of either IL-2 (aldesleukin) or RSLAIL-2 following adoptive cell transfer as described in Example 5.

It is claimed:

1. A method for treating a subject with melanoma, the method comprising:
   (i) administering to the subject with melanoma, autologous tumor-infiltrating lymphocytes (TILs) that have been harvested from the subject, cultured and expanded ex vivo, and
   (ii) administering to the subject an IL-2Rβ-activating amount of a long acting IL-2Rβ-biased agonist of Formula I,

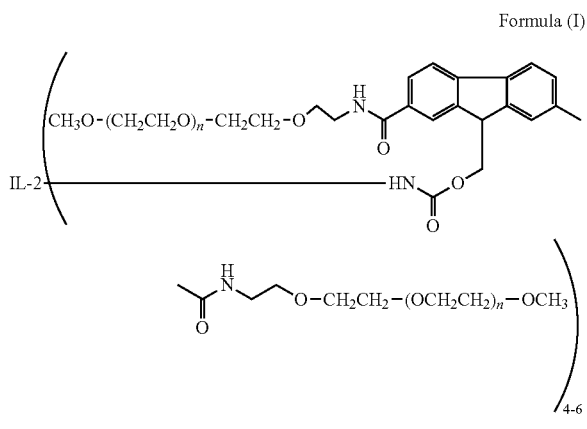

Formula (I)

wherein IL-2 is interleukin-2 and each "n" is independently an integer from about 3 to about 4000, or pharmaceutically acceptable salts thereof.

2. The method of claim 1, wherein step (i) and step (ii) are carried out sequentially, in either order, or substantially simultaneously.

3. The method of claim 1, wherein step (i) is carried out before step (ii).

4. The method of claim 1, wherein step (ii) is carried out before step (i).

5. The method of claim 1, wherein both steps (i) and (ii) are carried out substantially simultaneously.

6. The method of claim 5, wherein steps (i) and (ii) are both carried out on day 1 of treatment.

7. The method of claim 3, wherein step (ii) is carried out on any one of days 1 to 7 of treatment.

8. The method of claim 1, comprising a single administration to the subject of the autologous harvested, cultured and expanded tumor-infiltrating lymphocytes over the course of treatment.

9. The method of claim 1, comprising multiple administrations to the subject of an IL-2Rβ-activating amount of the long acting IL-2Rβ-biased agonist over the course of treatment.

10. The method of claim 1, wherein the autologous harvested, cultured and expanded tumor-infiltrating lymphocytes are administered by infusion.

11. The method of claim 1, wherein the subject is human.

12. The method of claim 1, wherein the cancer is metastatic melanoma.

13. The method of claim 1, wherein the IL-2 of Formula (I) is aldesleukin.

14. The method of claim 1, wherein each "n" is an integer from about 40 to about 550.

15. The method of claim 14, wherein each "n" is about 227.

16. The method of claim 14, wherein the long acting IL-2Rβ-biased agonist comprises no more than about 10% (molar amount) of compounds in accordance with Formula II,

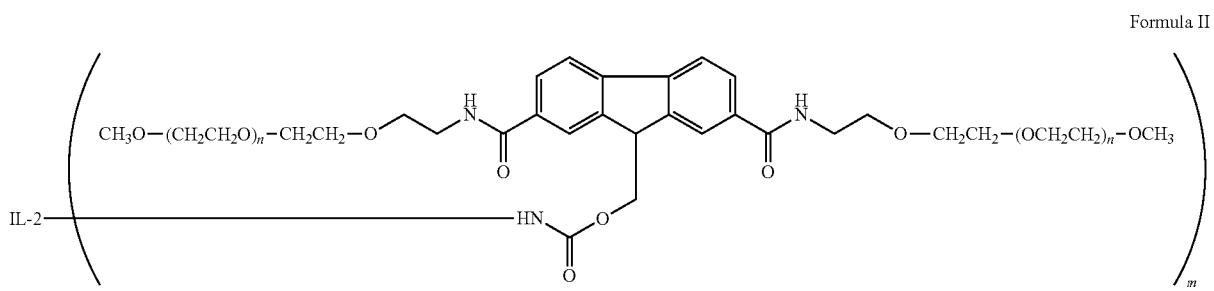

Formula II wherein IL-2 is interleukin-2, "m" is an integer selected from the group consisting of 1, 2, 3, 7 and >7, or pharmaceutically acceptable salts thereof.

17. The method of claim 14, wherein the long acting IL-2Rβ-biased agonist in accordance with Formula I possesses on average about six branched polyethylene glycol moieties releasably attached to IL-2.

18. The method of claim 1, wherein the long acting IL-2Rβ-biased agonist is initially administered within 4 days of administering to the subject the autologous harvested, cultured and expanded tumor-infiltrating lymphocytes.

19. The method of claim 1, wherein the long acting IL-2Rβ-biased agonist is administered by injection.

20. The method of claim 14, wherein the method is effective to result in a greater number of melanoma tumor-specific effector T cells retained at a melanoma tumor site of the subject when compared to the number of melanoma tumor-specific effector T-cells retained at a melanoma tumor site of the subject upon treatment of the subject with step (i) alone absent administration of the long-acting IL-2Rβ-biased agonist, or, when compared to the number of tumor-specific effector T-cells retained at a melanoma tumor site of the subject upon treatment of the subject with the harvested, cultured and expanded autologous tumor-infiltrating lymphocytes from step (i) in combination with administration of interleukin-2 dosed to achieve a comparable number of IL-2 equivalents, when measured at a time point that is at least 10 days following the initial administration of the long-acting IL-2Rβ-biased agonist.

21. The method of claim 20, wherein the time point is at day 10, 11, 12, 13, 14 or 15 following the initial administration of the long-acting IL-2Rβ-biased agonist.

22. The method of claim 1, wherein the method results in a beneficial response treatment that is enhanced over the response to treatment observed when administration is carried out according to either step (i) or step (ii) alone.

23. The method of claim 21, wherein the beneficial response to treatment is based on a suitable animal model of melanoma.

24. The method of claim 1, wherein the method of treatment is effective to inhibit accumulation of regulatory T cells selected from the group consisting of CD4+ Tregs, CD25+ Tregs, and FoxP3+ Tregs in a melanoma tumor of the subject by an amount that is enhanced over that observed upon treatment of the subject with step (i) alone absent administration of the long-acting IL-2Rβ-biased agonist, or, upon treatment of the subject with the autologous harvested, cultured and expanded tumor-infiltrating lymphocytes from step (i) in combination with administration of interleukin-2 dosed to achieve a comparable number of IL-2 equivalents.

25. The method of claim 24, wherein said inhibition of accumulation of regulatory T cells is evaluated in an in vivo melanoma model.

* * * * *